(12) United States Patent
Giraud et al.

(10) Patent No.: US 9,872,813 B2
(45) Date of Patent: Jan. 23, 2018

(54) MASSAGING APPLIANCE EQUIPPED WITH INTERCHANGEABLE AND DISTINGUISHABLE MASSAGING HEADS

(71) Applicant: SEB S.A., Ecully (FR)

(72) Inventors: Camille Giraud, Lyons (FR); Monique Paget, Optevoz (FR); Franck Mandica, Francheville (FR)

(73) Assignee: SEB S.A., Ecully (FR)

( * ) Notice: Subject to any disclaimer, the term of this patent is extended or adjusted under 35 U.S.C. 154(b) by 420 days.

(21) Appl. No.: 14/646,608

(22) PCT Filed: Oct. 17, 2013

(86) PCT No.: PCT/FR2013/052483
§ 371 (c)(1),
(2) Date: May 21, 2015

(87) PCT Pub. No.: WO2014/080103
PCT Pub. Date: May 30, 2014

(65) Prior Publication Data
US 2015/0305969 A1 Oct. 29, 2015

(30) Foreign Application Priority Data

Nov. 22, 2012 (FR) ...................................... 12 61107

(51) Int. Cl.
| | |
|---|---|
| *A61H 11/00* | (2006.01) |
| *A61H 15/00* | (2006.01) |
| *A61H 7/00* | (2006.01) |
| *A61H 23/02* | (2006.01) |
| *A61N 1/30* | (2006.01) |
| *A61N 5/06* | (2006.01) |

(52) U.S. Cl.
CPC ......... *A61H 15/0085* (2013.01); *A61H 7/005* (2013.01); *A61H 7/007* (2013.01);
(Continued)

(58) Field of Classification Search
None
See application file for complete search history.

(56) References Cited

U.S. PATENT DOCUMENTS 5,103,809 A  4/1992 Deluca et al.
2007/0270727 A1* 11/2007 Khorassani Zadeh . A61H 1/008
601/120
(Continued)

FOREIGN PATENT DOCUMENTS

CN        201750912 U   2/2011
EP          1925275 A2   5/2008
(Continued)

*Primary Examiner* — Stephen R Crow
(74) *Attorney, Agent, or Firm* — The Webb Law Firm

(57) ABSTRACT

Provided is a massaging appliance comprising: a body which has drive means, at least one type of massaging head which comprises at least two massaging elements, a transmission mechanism which allows the massaging elements to be activated under the action of the drive means, fitting means which are designed to fit at least one type of massaging head in a removable manner on the body, distinguishing means for distinguishing the type of massaging head fitted on the body and control means for controlling said massaging appliance which, depending on which type of massaging head is distinguished, are designed to act on the drive means so as to control the movement of at least two elements of the massaging head.

21 Claims, 18 Drawing Sheets

(52) U.S. Cl.
CPC .. *A61H 23/0245* (2013.01); *A61H 2015/0014* (2013.01); *A61H 2015/0057* (2013.01); *A61H 2201/0107* (2013.01); *A61H 2201/10* (2013.01); *A61H 2201/105* (2013.01); *A61H 2201/1654* (2013.01); *A61H 2201/1685* (2013.01); *A61H 2201/5007* (2013.01); *A61H 2201/5058* (2013.01); *A61H 2201/5092* (2013.01); *A61H 2205/022* (2013.01); *A61N 1/30* (2013.01); *A61N 2005/0659* (2013.01); *A61N 2005/0663* (2013.01)

(56) References Cited

U.S. PATENT DOCUMENTS

| | | |
|---|---|---|
| 2008/0125682 A1 | 5/2008 | Bonneyrat |
| 2008/0209650 A1 | 9/2008 | Brewer et al. |
| 2011/0184499 A1 | 7/2011 | Radi |
| 2015/0005682 A1* | 1/2015 | Danby .............. A61H 23/0254 601/101 |
| 2015/0305969 A1* | 10/2015 | Giraud ................... A61H 7/005 601/18 |
| 2016/0175185 A1* | 6/2016 | Buchner Santos .............. A61H 15/0085 601/113 |
| 2016/0256348 A1* | 9/2016 | Giraud ............. A61H 15/0085 |
| 2016/0262973 A1* | 9/2016 | Giraud ............. A61H 15/0078 |
| 2016/0271009 A1* | 9/2016 | Giraud ................ A61H 23/006 |

FOREIGN PATENT DOCUMENTS

| | | |
|---|---|---|
| KR | 101004373 B1 | 12/2010 |
| WO | 2010012857 A1 | 2/2010 |

* cited by examiner

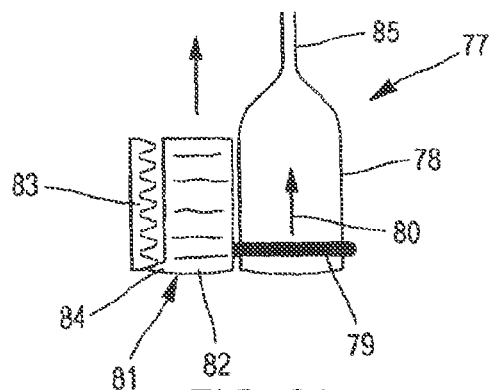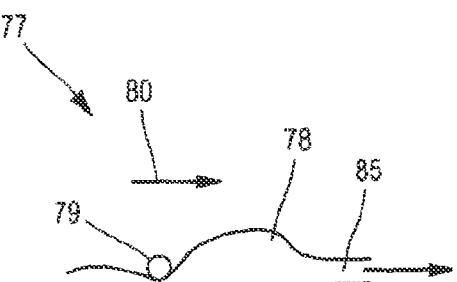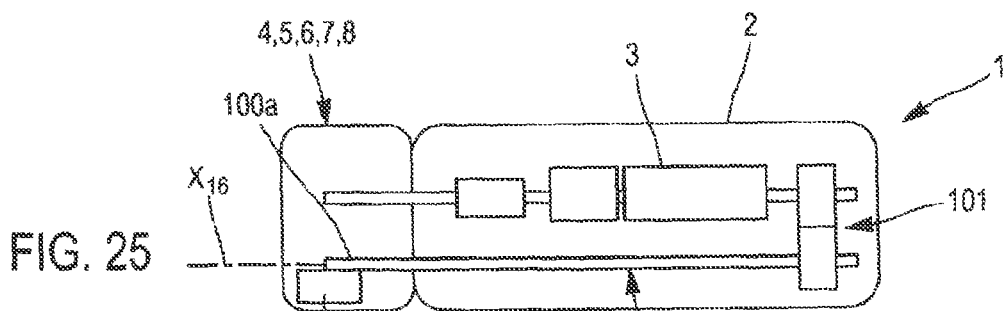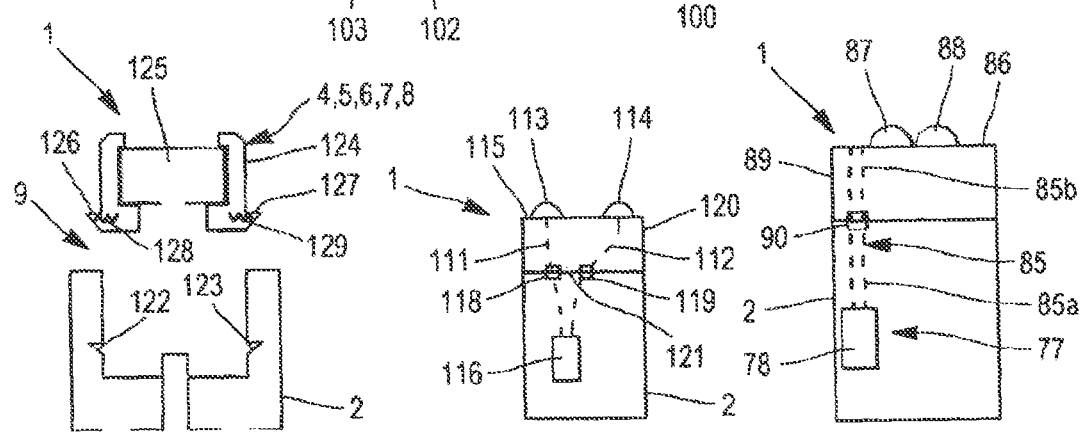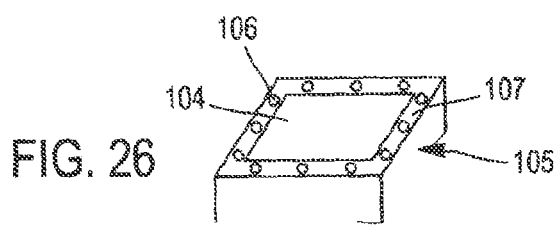

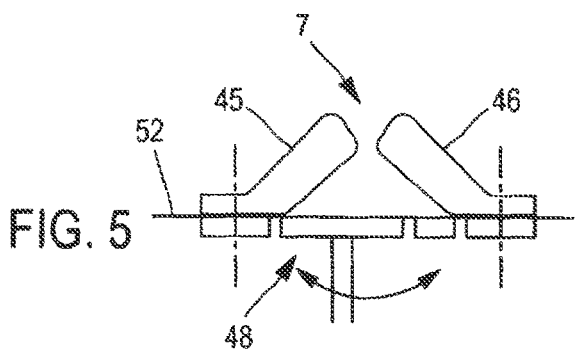
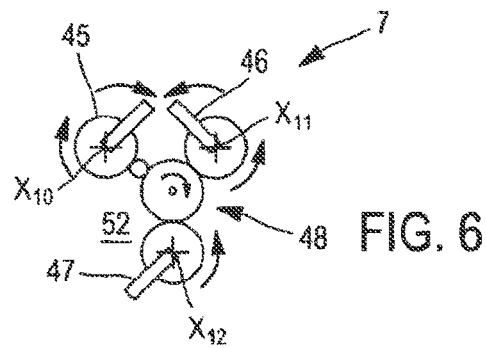
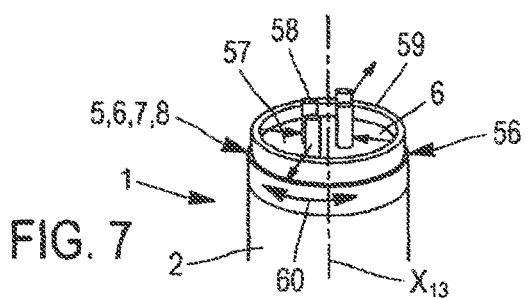
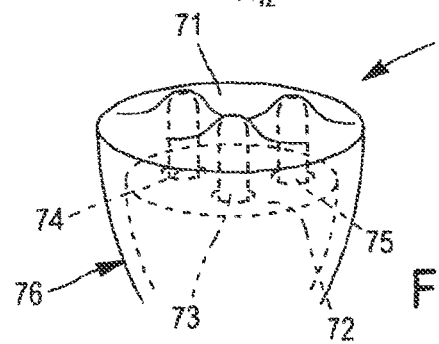
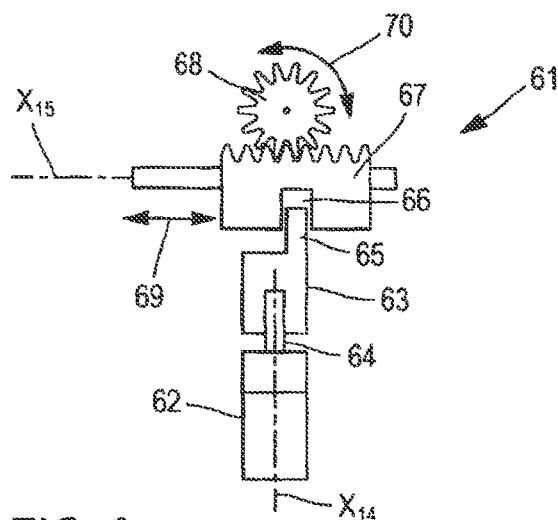
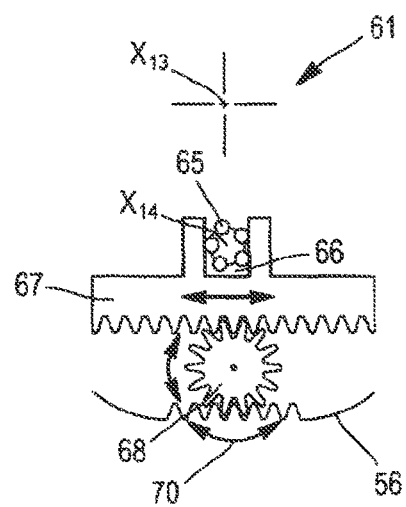
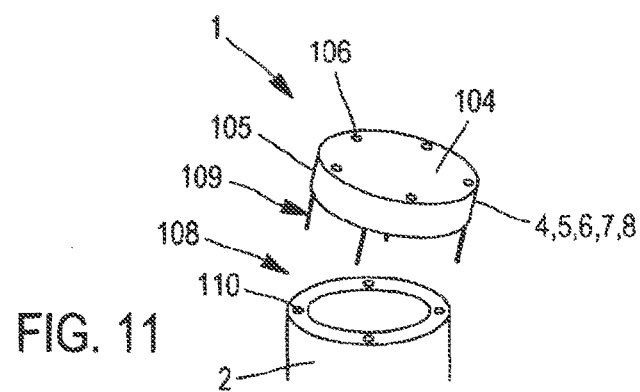

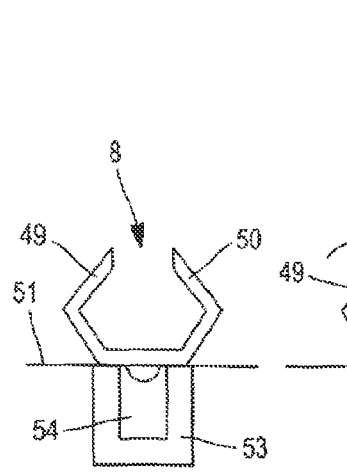
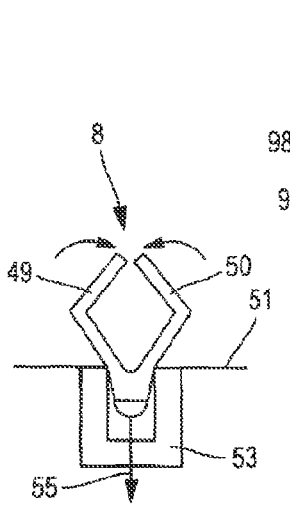
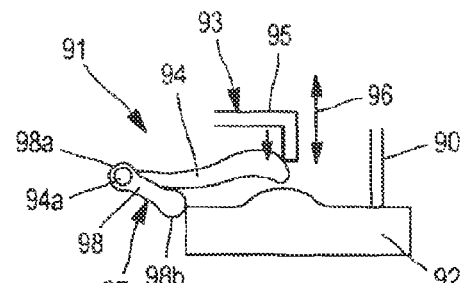
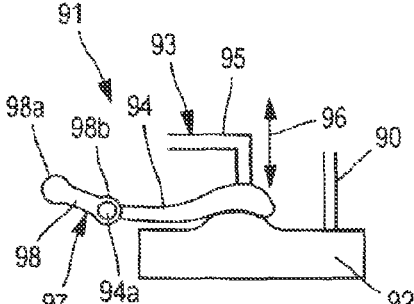
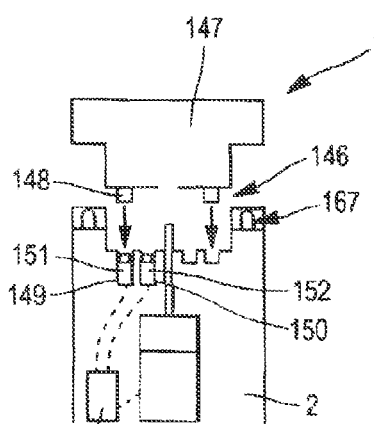
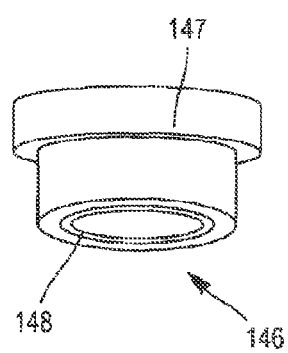
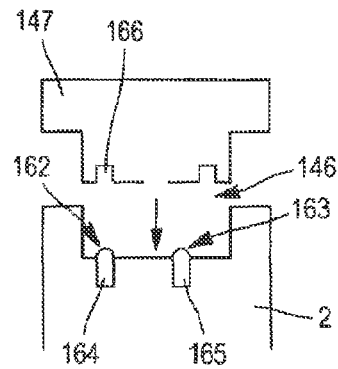
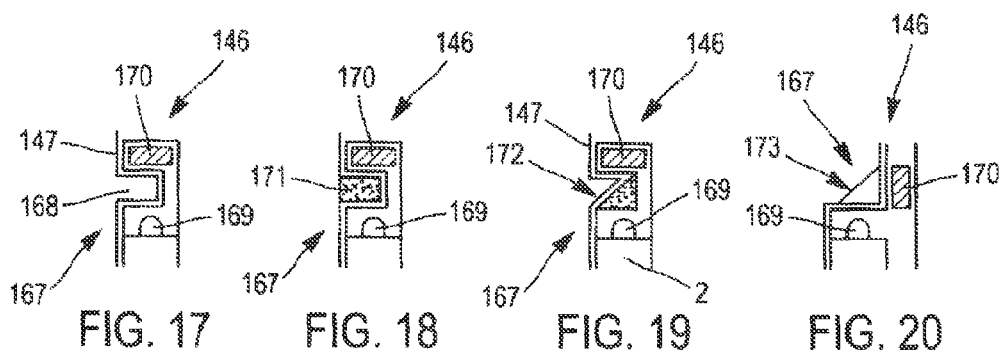

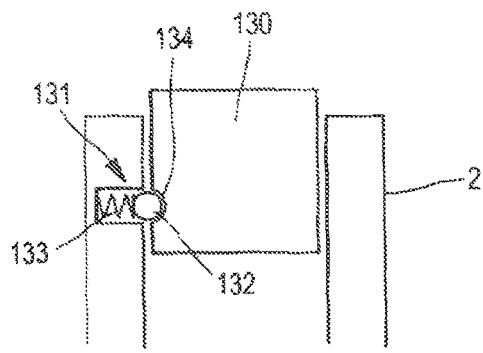
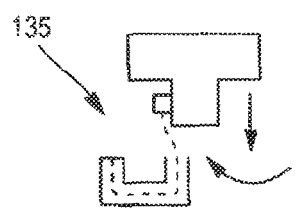
FIG. 29  FIG. 30
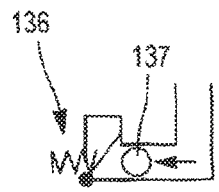 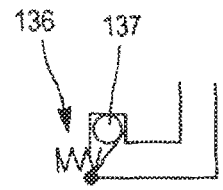
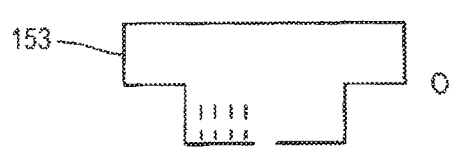
FIG. 31  FIG. 32
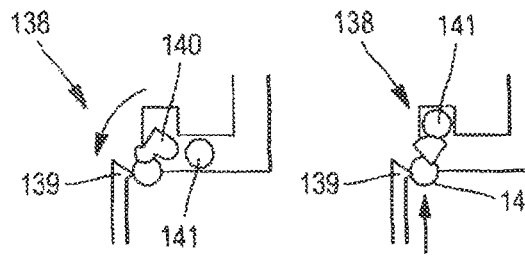
FIG. 33  FIG. 34
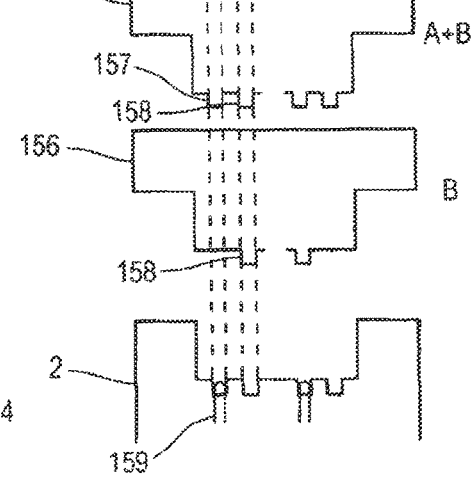
FIG. 35  FIG. 36
FIG. 37

MASSAGING APPLIANCE EQUIPPED WITH INTERCHANGEABLE AND DISTINGUISHABLE MASSAGING HEADS

CROSS-REFERENCE TO RELATED APPLICATIONS

This application is the United States national phase of International Application No. PCT/FR2013/052483 filed Oct. 17, 2013, and claims priority to French Patent Application No. 1261107 filed Nov. 22, 2012, the disclosures of which are hereby incorporated in their entirety by reference.

FIELD OF THE INVENTION

This invention pertains to the field of skin treatment appliances, and particularly facial skin. The appliance described in the invention is used, at a minimum, to massage the skin in order to tone it. The massaging appliance described in the invention will be used in households consisting of people who wish to look after their appearance by sculpting, firming and rejuvenating their skin, and particularly their facial skin.

DESCRIPTION OF RELATED ART

Skin massaging appliances generally consist of a body, equipped with a driving means and a massaging head comprised of massaging elements configured to be propelled by the driving means, via a transmission mechanism. Among the existing prior art, there is known patent EP 1 925 275 B1 which, in addition to the aforementioned characteristics, discloses a means of attachment and a transmission mechanism, that allows the massaging head to be replaced easily and exchanged for a new or different one, and the transmission mechanism's design also allows the massaging head to be attached to the body, such that the axis of the head's angle of orientation with respect to the axis of the body, can be different.

The purpose of this invention is to design a skin massaging appliance that allows different types of massaging heads to be attached to the body of the massaging appliance, while optimizing the performance and characteristics of the massaging appliance in order to adapt it optimally to the function of the type of massaging head used.

SUMMARY OF THE INVENTION

To this end, the invention pertains to a massaging appliance, consisting of a body that has a driving means, at least one type of massaging head comprised of at least two massaging elements, a transmission mechanism that activates the massaging elements under the force of the driving means, a means of attachment that is configured to attach, in a removable manner, at least one type of massaging head to the body, a means of distinguishing the type of massaging head attached to the body and a means of controlling said massaging appliance, which, depending on the type of massaging head distinguished, is configured to act upon the driving means, so as to control the movement of at least two elements in the massaging head.

Thus, the appliance can detect the type of head attached to the body and adapts according to the type of massaging head, for example by adjusting the speed of the driving means, by controlling either of the elements of the driving means, among others, to ultimately control the movement of at least two elements of any massaging head. This offers the advantage of being able to adapt massaging heads with functional features that differ widely from one another.

In the massaging appliance described in the invention, the means of control is configured to act upon the driving means and change its action according to the type of massaging head attached to the body. Thus, for example, the activation speed of the massaging elements in the massaging head can be adjusted, making it possible to optimize the usage conditions of the massaging head. This also makes it possible to arrange, on the body, more or less complex driving means, configured to activate different types of massaging heads with widely varying design features and to control this driving means according to whichever massaging head is distinguished.

In the invention, the control means of said massaging appliance may be configured to act upon the driving means, so as to control, in a coordinated manner, a movement of the aforementioned at least two massaging elements. The movement is coordinated because the action of the massaging elements is driven by a single transmission mechanism from the drive shaft of the driving means, and the transmission mechanism acts in a coordinated manner upon each of the massaging elements. The movement of the at least two massaging elements can be "coordinated" but not necessarily identical. For example, as we will see below, for the "Jacquet pinching" head, the two roller massaging elements are spun around their axis of symmetry in the same spin direction, but at a different speed. The movement between the at least two massaging elements may vary, for example, in terms of speed, spin direction and lateral direction.

In the invention, the means of control of said massaging appliance may be configured to act upon the driving means so as to spin each of said at least two massaging elements. The movement can be different, in that it is a spin in only one direction, around an axis of symmetry of the element, for example, or an oscillating spin. The two elements may be spinning in the same direction or in a different direction.

In the invention, the massaging elements are chosen from among the set consisting of: massaging tip, massaging finger, massaging roller, work head and massaging ball. All of these elements are made of a rather rigid material (metal, steel, plastic, etc.), but they can be covered only in a soft silicone-type material to adhere to the skin better, if necessary. All of these elements are offered so that the user feels pressure and a targeted massage on the skin.

In the invention, the means of controlling said massaging appliance is configured to act upon the driving means so as to control at least one of the following parameters of said at least two massaging elements: spin speed, spin direction and oscillation frequency. One or more parameters may be controlled at the same time. Consequently, several types of massage are available to the user.

In the massaging appliance described in the invention, it contains a system or means of emitting waves, in which the control means is configured to act upon the wave-emitting system according to the type of massaging head attached to the body.

This wave-emitting means can be positioned on the body, and the appliance contains a means of transferring waves from the wave-emitting means to the massaging head attached to the body. This makes it possible to have skin treatment functions that are complementary to those of the massaging head. These waves can be electromagnetic waves, and particularly visible light waves, or in the infrared field, or they can be sound waves, such as ultrasound. This also makes it possible to work the user's skin in a complementary manner. In one proposed example of implementation, this means of emitting light waves is among at least one of the following wavelengths: visible wavelength, including red (roughly 630 nm) and orange (roughly 590 nm), and infrared wavelength (roughly 830 nm). In one preferred but non-limiting method of implementation, the massaging appliance contains a light system positioned on the body and a means of transferring the light from the light system to the massaging head.

In the massaging appliance described in the invention, the control means is configured to act upon the wave-emitting system and change the waves according to the type of massaging head attached to the body. This may involve changing the wavelength(s) and/or intensity and/or frequency of the emitted waves, depending on the type of massaging head attached to the body.

In the massaging appliance described in the invention, the wave-emitting means may be positioned on the body, and a means of transferring the waves, from the wave-emitting system to the massaging head. This makes it possible, in particular, to provide a compact, economical appliance.

In the invention, the wave-emitting means may contain electroluminescent diodes. The appliance may contain between 2 and 20 diodes in all, orange and red. The appliance may contain infrared diodes that can produce heat to achieve an "instant radiance" effect. These various diodes may be activated by type only (orange LEDs only, red LEDs only, infrared LEDs only) for a particular massaging head, or even also for a phase of treatment of a particular head.

Indeed, in the massaging appliance described in the invention, the control means can be configured to act simultaneously upon the wave-emitting system and the driving means, so as to control the movement of at least two elements of the massaging head, and to do so depending on the type of massaging head distinguished, to create at least two different phases of skin treatment during the treatment.

In a first method of implementing the massaging appliance described in the invention, the distinguishing means consists of mechanical sensors positioned on at least one type of massaging head and the body, which are configured to transmit information to the control means, depending on the type of massaging head attached to the body. The mechanical sensors cover every mechanical sensor, including electrical contacts that come into contact with one another when the massaging head is attached to the appliance.

In a second method of implementing the massaging appliance described in the invention, the distinguishing means consists of magnetic sensors positioned on at least one type of massaging head and the body, which are configured to transmit information to the control means depending on the type of massaging head attached to the body. They cover every type of magnetic sensor, such as a reed switch in combination with a magnet (or electromagnet or Hall effect sensor).

In a third method of implementing the massaging appliance described in the invention, the distinguishing means consists of optical sensors positioned on at least one type of massaging head and the body, which are configured to transmit information to the control means depending on the type of massaging head attached to the body. They cover every type of optical sensor, such as light sensors and optical, translucent, transparent and reflective surfaces. They are positioned at the bottom of the hole in the handle portion of the appliance or on its sides.

The appliance cannot be turned on if no head is correctly attached to the body and distinguished by the distinguishing means.

In the massaging appliance described in the invention, it includes a cosmetic product dispensing system positioned on the body and a means of transferring the product from the body to the massaging head. This also makes it possible to provide skin treatment functions that are complementary to those of the massaging heads. Depending on the configuration of the dispensing system, the cosmetic product can be dispensed naturally, manually and/or automatically.

In one method of implementation, the massaging appliance described in the invention includes a means of activating the cosmetic product dispensing system, which is configured to allow said dispensing system to operate in manual mode or in automatic mode. This allows complete freedom of use of the massaging appliance, as the user can thus choose to perform a cosmetic treatment to supplement the one obtained with the massaging head.

In the massaging appliance described in the invention, the means of control is configured to act upon the cosmetic product dispensing system and to change at least the dispensing of the cosmetic product depending on the type of massaging head attached to the body. This makes it possible to perform a cosmetic treatment that is appropriate for the different massaging heads.

In the massaging appliance described in the invention, the means of attachment includes a system for detecting that the massaging head is correctly attached to the body. This ensures that the massaging appliance will be used under the proper conditions.

In the massaging appliance described in the invention, it contains a means of connection between the driving means and the transmission mechanism, which are configured to be independent of the angle of orientation of the transmission mechanism with respect to the driving means, when the massaging head is attached to the body. Thus, it is possible to attach massaging heads to the body with different orientations, as some heads may, for example, be positioned as an extension of the body when attached, while other heads are positioned at a 45° angle to the body.

In one method of implementing the massaging appliance described in the invention, one of the massaging head types contains an application surface and the massaging elements are comprised of at least two massaging tips that extend perpendicularly toward the exterior of the application surface, the massaging tips being defined on the application surface according to virtual concentric circles with a center C and, in which a transmission mechanism is configured to bring the massaging tips close together and/or, inversely, to spread the massaging tips apart, by moving said massaging tips laterally in one direction and/or the other, along trajectories that meet in the center C. This type of massaging head can perform a pinching of the skin.

In one method of implementing the massaging appliance described in the invention, one of the massaging head types contains an application surface and the massaging elements are comprised of two massaging tips that extend perpendicularly toward the exterior of the application surface, as the transmission mechanism is configured to spin the two tips, along an axis that is perpendicular to the application surface, with an oscillating movement. This type of massaging head can perform precision work around the eyes and mouth, in particular, by applying the massaging tips perpendicular to the skin, to perform a spinning pinching effect or, parallel to the skin to perform a sculpting, firming effect.

In one method of implementing the massaging appliance described in the invention, the massaging head includes an application surface, and the massaging elements are comprised of three massaging tips that are inclined toward the exterior with respect to the application surface, as the transmission mechanism is configured to spin or oscillate the three massaging tips, along three respective fixed axes, perpendicular to the application surface. This type of massaging head can perform a light pinching of the skin.

In one method of implementing the massaging appliance described in the invention, the massaging head has an application surface, and the massaging elements are comprised of at least two massaging fingers that extend toward the exterior of the application surface, as the massaging fingers and the transmission mechanism are configured to form a claw. This type of massaging head can perform a pinching of the skin.

In these various methods of implementing the massaging appliance described in the invention, with massaging tips or massaging fingers, the massaging head includes a soft skin that covers the massaging elements. This prevents the massaging tips or the massaging fingers from feeling too aggressive, and allows them to better grip the skin through surface contact on the skin.

In one method of implementing the massaging appliance described in the invention, the massaging head has a crown extending perpendicular to the application surface, and the transmission mechanism is configured to propel the crown in an oscillating movement around an axis that is perpendicular to the application surface. This makes it possible to grip the skin well and to perform complex movements on the skin, in combination with massaging tips or massaging fingers.

In one method of implementing the massaging appliance described in the invention, the massaging head has an application surface and the massaging elements are comprised of two massaging rollers positioned along two parallel longitudinal axes, with space between them, partially extending beyond the exterior of the application surface and, in which a transmission mechanism is configured to propel the synchronized, inverse spinning of the two rollers, such that, when viewed along a plane running perpendicular to the two axes, the portion of the massaging roller located on the left that extends beyond the application surface, spins in a trigonometric direction, and the portion of the massaging roller located on the right that extends beyond the application surface, spins clockwise. This type of massaging head can perform a folding of the skin.

In the invention, the massaging appliance may include a massaging head containing two massaging elements comprised of two parallel massaging rollers that are mobile and spin on themselves along two parallel spinning axes between them and on the application surface, apart from one another due to being separated by a work zone, in which a first roller having at least one paddle that protrudes radially from the surface of the first roller, and the second roller with a smooth type surface, the transmission mechanism spinning the rollers in the same direction, the first roller going from the exterior of the work zone toward the interior of the work zone, and the second roller going from the interior of the work zone toward the exterior of the work zone, when viewed from the exterior of the massaging head. This head automates the hand actions of professional estheticians known as "Jacquet pinching."

In the invention, the massaging appliance may include a massaging head (1) with a pressure element intended to be applied against the face, that defines a pressure surface, above the pressure element at least one massaging element consisting of a massaging finger, each having one work head that comes into contact with the face, and each one being able to move between: a retracted position (R) in which the work head is located below the pressure surface toward the interior of the massaging head, an extended position (E) in which the work head is located above the pressure surface toward the exterior of the massaging head, a means of maneuvering each massaging finger to be connected to the transmission mechanism and designed to move each of the massaging fingers between its positions of extension (E) and retraction (R) in an alternating manner. This head automates the hand actions of professional estheticians known as tapping.

For this tapping massaging head, when the appliance is equipped with a means of emitting waves, the control means can be configured to recognize the head, to activate the system emitting visible orange light waves. This tapping-orange light combination performs an action on the surface epidermis of the skin.

In the invention, the massaging appliance may include a massaging head that has a pressure element intended to be applied against the face, that forms a pressure crown defining, on the one hand, a pressure surface that is part of a pressure plane and, on the other hand, a work zone located inside the pressure crown, inside the pressure crown and in the work zone, at least one massaging element consisting of a work head with a work surface protruding from the pressure plane, a maneuvering means to be connected to the transmission mechanism and designed to spin each work head along at least one axis of rotation ($\Delta$, $\Delta'$) offset from the center of the corresponding work surface.

For this head that massages by means of a moving work zone inside a pressure crown, when the appliance is equipped with a means of emitting light waves, the control means is configured to, upon distinguishing the head, activate the infrared light wave emitting system. This tapping-orange light combination can perform an action deep in the dermis.

In the massaging appliance described in the invention, it includes a transcutaneous iontophoresis treatment device that is configured to transmit onto the skin, when said massaging appliance is applied, a current that can improve and/or accelerate the penetration of a cosmetic product, which can either be dispensed by the cosmetic product dispensing system described above, or applied directly to the skin by the user. Iontophoresis is a treatment that was initially developed for applying medication to the skin, particularly for sports medicine, but is also now considered for better penetration of cosmetics. In one method of implementation, this transcutaneous iontophoresis device contains at least two electrodes with differing electric potential that can be positioned on the massaging tips or rollers and/or on the application surface of the massaging head. The settings of the massaging appliance in the invention, particularly when it also contains a cosmetic product dispensing system, can perform the transcutaneous iontophoresis treatment before and/or during the application of the cosmetic product. These settings will be dependent on distinguishing the massaging head attached to the body.

In one possible "iontophoresis" program, a specialized cosmetic is applied, either manually or by an appropriate head, and then a special head with electrodes is connected, and then the appliance will be moved while maintaining contact for continuous treatment over the whole zone, or held in one zone with a countdown timer and an indicator that tells the user when to change.

In one characteristic of the invention, the massaging appliance has, on its body, a user interface (UI) with a screen that displays at least one of the following kinds of data: treatment duration (total, elapsed, remaining), treatment phases, and the name of the head distinguished.

The UI may also include control buttons (directly on the screen or mechanical actuators on the casing) so that the user can set and choose from among the offered programs, to adjust the treatment according to the user's wishes (within the limits defined by the automatic distinguishing means). The treatment can be adjusted using the settings.

The UI can give the user a choice between two different programs, once the massaging head is properly attached and distinguished. The UI can give the user a choice between a single program with two different levels of intensity for the same head, so the user can choose a high or low intensity of the massage or waves emitted.

This UI can also be used to semi-automatically direct the changing of the head on the appliance. For example, a program may begin with an initial massaging phase using a first head, and at the end of the initial phase, the UI instructs the user to replace it in order to begin a second phase. Thus, the head is automatically designated via the control means and the user changes the head, which is then verified by the appliance before beginning the second treatment phase. This directing is done by the electronic control unit, which contains a timer.

Of course, other methods of implementing the distinguishing means can be considered on the massaging appliance, while remaining within the scope of the invention.

BRIEF DESCRIPTION OF THE DRAWINGS

The following description highlights the features and benefits of this invention, based on the drawings in which:

FIG. 4 depicts a removable attachment system between the massaging head and the body;

FIGS. 5 and 6 depict a massaging head with three inclined tips;

FIG. 7 depicts a crown on the massaging head;

FIG. 8 depicts a soft skin on the massaging head;

FIGS. 9 and 10 depict a transmission mechanism between the massaging head and the body;

FIG. 11 depicts a fiber optic connection system between the massaging head and the body;

FIGS. 12 and 13 depict a massaging head variant equipped with claws;

FIGS. 14 to 16 depict variants of the means of distinguishing the massaging head on the body;

FIGS. 17 to 20 depict variants of the means of distinguishing the massaging head on the body using optical sensors (167).

FIGS. 21 and 22 depict a cosmetic product dispensing system;

FIGS. 23 and 24 depict a variant of the cosmetic product dispensing system;

FIG. 25 depicts a vibration system on the massaging appliance;

FIG. 26 depicts light diodes on the massaging head;

FIG. 27 depicts a transcutaneous iontophoresis treatment device on the massaging appliance;

FIG. 28 depicts a dispensing system positioned between the body and the massaging head;

FIGS. 29 to 36 depict implementation variants of the locking system between the massaging head and the body;

FIG. 37 depicts the distinguishing of different massaging heads when they are attached to the body.

FIG. 38 is a cross section of a massaging appliance described in the invention, equipped with the tapping head, FIG. 39 is a perspective drawing of the removable massaging head with which the massaging appliance is equipped, FIG. 40 is a partially cutaway perspective view of the massaging head illustrated in FIG. 39, FIG. 41 is a cross section of another form of implementing a removable massaging head for a massaging appliance described in the invention, FIG. 42 is a partially cutaway perspective view of the massaging head illustrated in FIG. 41, FIG. 43 is a partially cutaway perspective view of another form of implementing the removable tapping head for a massaging appliance described in the invention, FIG. 44 is an elevation viewed from the side of another form of implementing a removable tapping head for a massaging appliance described in the invention.

FIG. 45 is a cross section of a massaging appliance described in the invention equipped with this interior work zone head, FIG. 46 is a perspective view of a first interior work zone head, FIG. 47 is a cross section of the interior work zone head in FIG. 46, FIG. 48 is a cross section of a second interior work zone head, FIG. 49 is a cross section of a third interior work zone head.

FIG. 50 is a cross section of a massaging appliance equipped with a Jacquet pinching head, FIG. 51 is a partially cutaway perspective view of the removable massaging head equipping the massaging appliance illustrated in FIG. 50, FIG. 52 is a perspective view of the massaging head illustrated in FIG. 51, FIG. 53 is a perspective view of another form of implementing a removable massaging head for a massaging appliance described in the invention, FIG. 54 is a cross section of the massaging head illustrated in FIG. 53, FIG. 55 is a perspective view of an alternative method to FIGS. 50 to 54 of implementing a smooth type surface roller in the illustrated invention, FIG. 56 is a perspective view of an alternative method to FIGS. 50 to 54 of a roller paddle described in the invention.

As illustrated in FIG. 1, the massaging appliance (1) has a body (2) inside of which there is a motor (3) electrically powered by a connection either to an external source of electricity, through an electrical plug and a low voltage transformer, or to an internal source of electricity, such as a rechargeable battery or disposable batteries. The massaging appliance (1) also has a gear motor positioned at the output of the motor (3) to reduce its rotation speed and adapt it as necessary for use. The massaging appliance (1) is configured to accept the attachment of different types of massaging heads (4, 5, 6, 7, 8, ta, bi and ja) illustrated in the drawings. To this end, the massaging appliance has a means of removable attachment (9) between the body (2) and the massaging head (4, 5, 6, 7, 8, ta, bi, ja). The massaging appliance also has, on its body, a user interface (UI) with a screen to display at least one of the following kinds of data: treatment duration (total, elapsed, remaining), treatment phase and the name of the head distinguished. The UI may also have control buttons (on the screen or mechanical on the casing) so the user can set and select one of the offered programs, to adjust the treatment as the user wishes (within the limits defined by the automatic distinguishing feature). This UI can also be used to semi-automatically direct the changing of the head on the appliance. For example, a program may begin with a phase using an initial head, and at the end of the first phase the UI instructs the user to replace it in order to begin a second phase. Thus, the head is automatically designated by the control means and the head is changed by the user, and then even verified by the appliance prior to initiating the second treatment phase.

In FIG. 2, the massaging head (4) has an application surface (9) and two massaging rollers (10, 11), one portion of which (10a, 11a) extends beyond the application surface (9). These rollers (7, 8) are positioned along two axes (X1, X2) that are parallel to one another. In this method of implementation, the motor (3) has a drive shaft connected to a sprocket wheel (13). Thus, the motor (3) spins the sprocket wheel (13) along Axis X3. This sprocket wheel (13) engages with another sprocket wheel (14) which is of the same design and positioned along Axis X4.

As illustrated in FIG. 2, the massaging head (4) has two jibs (15, 16). These jibs (15, 16) are assembled as a pivoting connection with Axes X3 and X4, respectively, by means of two shafts (17, 18). These jibs receive the rollers (10, 11), as a pivoting connection on Axis X1 and X2, by means of two shafts (19, 20) assembled as a pivoting connection onto said jibs (15, 16).

This massaging head (4) has two other sprocket wheels of the same design (not depicted). One of the sprocket wheels is connected to Roller 11 via Shaft 20, for example by means of flutes (not depicted) positioned between these elements, and engages with Sprocket Wheel 13. Likewise, the other sprocket wheel is connected to Roller 10 via Shaft 19, and engages with Sprocket Wheel 14. Thus, when Sprocket Wheel 13 is engaged via the motor (3), which spins in the direction indicated by Arrow 23, Sprocket Wheel 14 spins in the direction indicated by Arrow 24, thus engaging Roller 10, [which] is propelled in the direction indicated by Arrow 26, and Roller 11 in the direction of Arrow 25.

Figure 2:
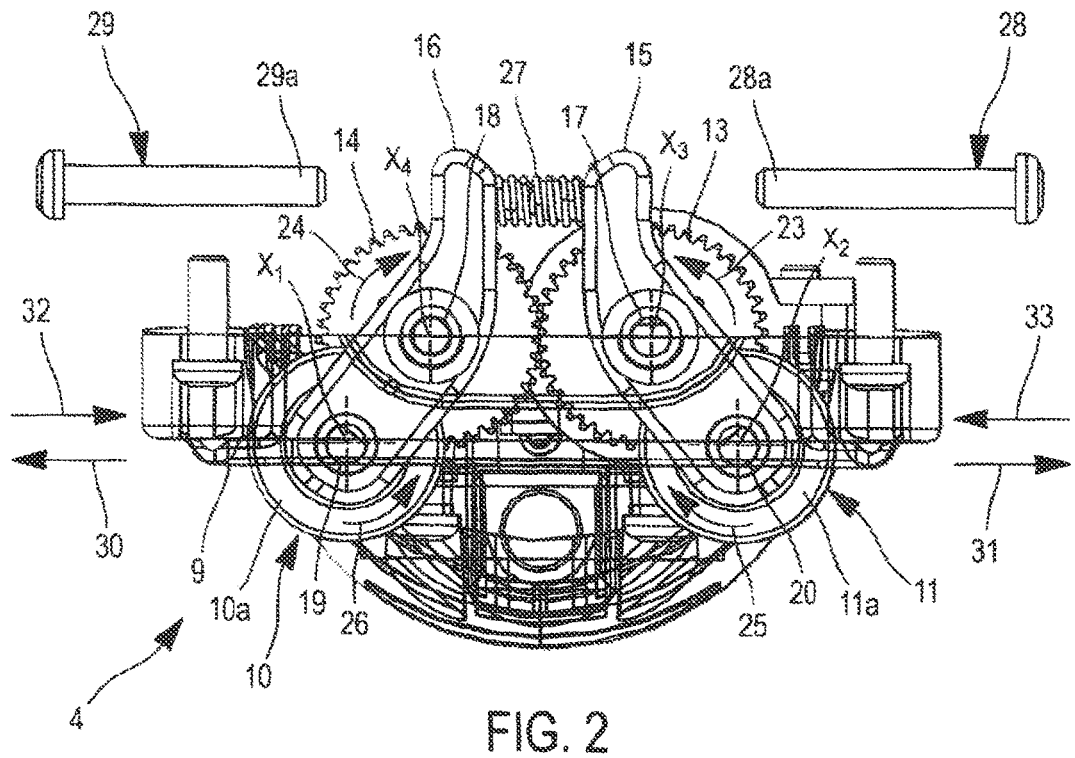
FIG. 2 depicts a massaging head with massaging rollers.

As depicted in FIG. 2, springs (27) are positioned between the two jibs (15, 16). In the initial position, these springs (27) act against the jibs (15, 16) and hold them in support against the ends (28a, 29a) of two adjustment screws (28, 29) positioned on the massaging head (4). Thus, the rollers (10 and 11) are spread apart from one another with a minimum gap in the initial position. In addition, by adjusting the screws (28, 29), the minimum gap between these two rollers (7, 8) can be changed. When Parts 10a and 11a of the rollers (10, 11) are applied to the skin, the opposite spinning directions of the rollers (10, 11) in the directions of the arrows (25, 26) form a fold in the skin. The force exerted by the skin on these rollers, when these forces are greater than the forces exerted by the springs (27), thereby compress these springs (27) and spread the rollers apart in the directions of Arrows 30 and 31 depicted in FIG. 2. On the other hand, if these forces exerted by the skin on the rollers (10, 11) are lesser than the forces exerted by the springs (27), these springs (27) slacken and return the rollers (10, 11) in the directions indicated by Arrows 32 and 33 depicted in FIG. 2, until a position of equilibrium is reached.

Implementation variants of transmission mechanisms on the attachment head (4), functioning according to the same principle, can be considered while still remaining within the scope of the invention.

Figure 3:
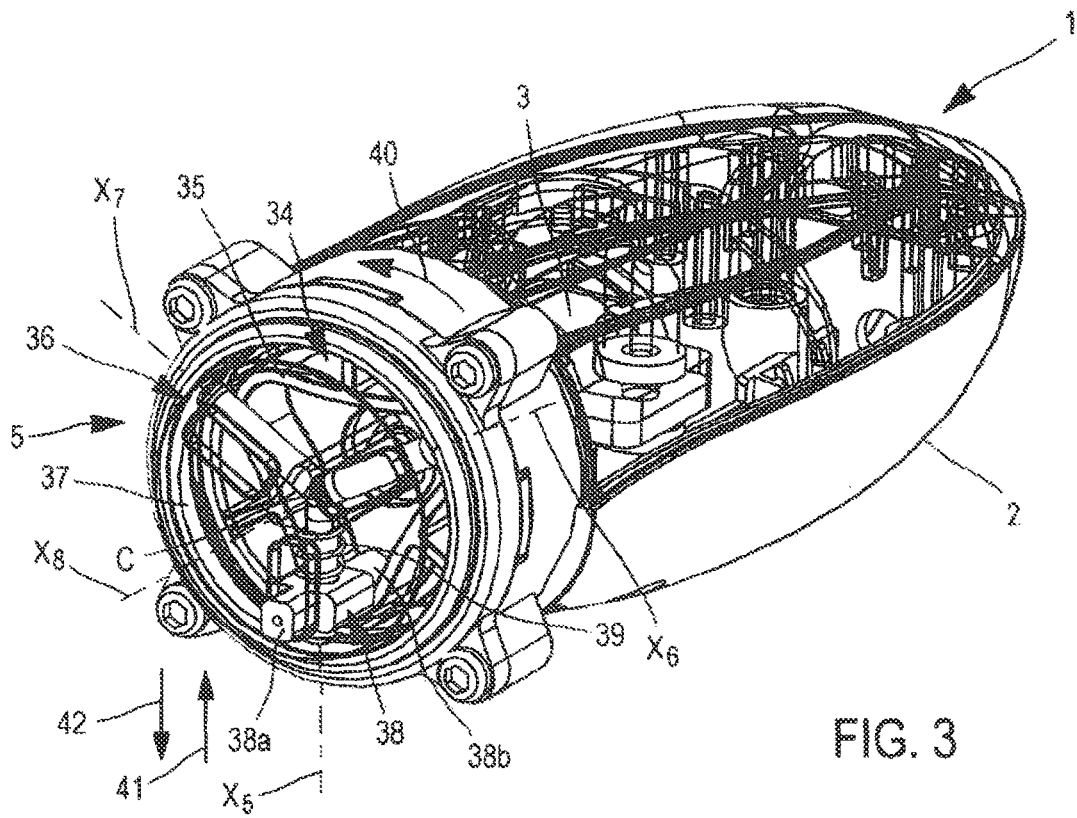
FIG. 3 depicts a massaging head with massaging tips.

As depicted in FIG. 3, the massaging head variant (5) has a transmission piece (34) with a triangular-shaped cam (35). A cylindrical-shaped guide piece (36) has an application surface (37) that is positioned parallel to the surface of the skin while the massaging appliance (1) is in use.

In FIG. 3, only one massaging tip (38) is depicted. However, it is understood by looking at FIG. 3 that the massaging head (5) in this method of implementation has three identical, uniformly distributed massaging tips. The massaging tip (38) has an external portion (38a) that extends perpendicular to the application surface (37), toward the exterior of it. This external portion (38a) comes in contact with the user's skin when the massaging appliance (1) is applied.

As depicted in FIG. 3, the guide piece (36) makes it possible to rise laterally along Axis X5 on the guide piece (36). The same is true for the tips, along Axes X6 and X7. The motor (3) propels the spinning of the guide piece (36) along Axis X8.

As depicted in FIG. 3, the massaging tip (38) has an internal portion (38b). When the massaging head (5) is attached to the body (2), this internal portion (38b) is positioned inside the cam (35) of the transmission piece (9). This internal portion (38b) is held against the cam (35) by means of a spring (39). When the guide piece (36) is propelled to spin around Axis X8 in the direction indicated by Arrow 40, the massaging tip (38) spins with it. The cam (35) exerts a force against the internal portion (69) and pushes the massaging tip (38) in the direction indicated by Arrow 41 on a first angular portion, which moves the massaging tip (21) laterally along Axis X5 in the direction indicated by Arrow 41, toward the center (C) defined by the intersection of Axis X8 with Axes X5, X6 and X7. Then, on a second angular portion, the cam (35) ceases to exert this force on the internal portion (38b). The spring (39), which performs a return function, pushes against the massaging tip (38) in the direction of Arrow 42 and moves it laterally along Axis X5 in the direction of Arrow 42, to distance it from the center (C). The spinning of the guide piece (36) around Axis X8, combined with the lateral movement of the massaging tip (38) along Axis X5 thus allows this massaging tip (38) to approach and then move away from the center (C), making a circular lateral movement or curvilinear movement. It is understood that the two other massaging tips undergo the same movements in synchronization with Massaging Tip 38. Thus the three massaging tips (38) are positioned on a single virtual circle with a center (C) and move in a curvilinear motion, passing through the center (C). This performs a spinning pinching of the skin by means of the massaging head (5).

Implementation variants with four tips can be considered for the massaging head (5). One could also consider a fixed guide piece and a transmission piece spinning around Axis X8, in which case the massaging tips will move radially toward the center (C) to move away from or approach it. One could also consider multiple variants of cams, depending on the number of tips present.

Figure 1:
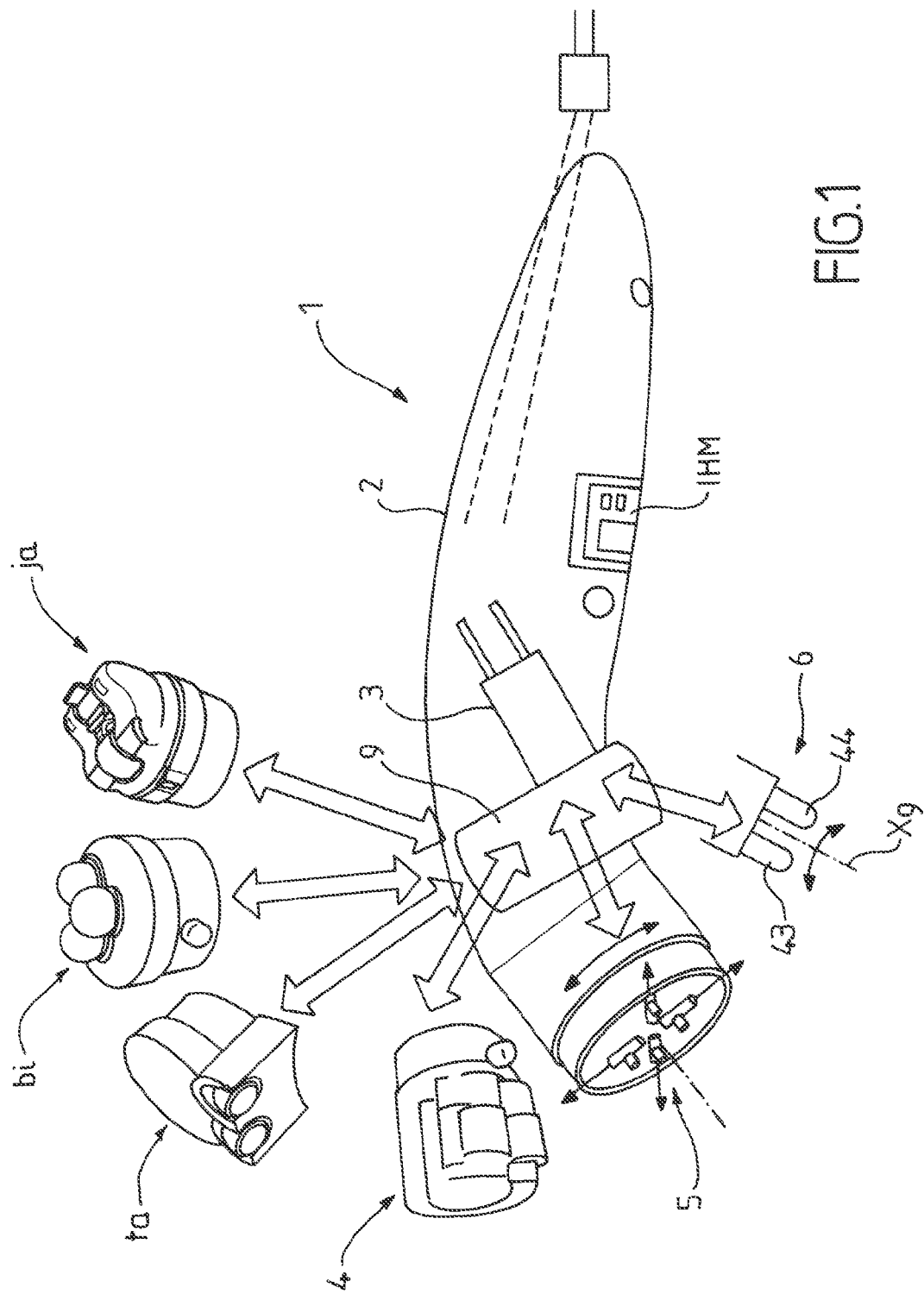
FIG. 1 depicts a massaging appliance described in the invention that can receive various designs of massaging heads.

Other massaging head variants can also be considered. In FIG. 1, we see that the massaging head (6) has two tips (43, 44) that are propelled to spin or oscillate around Axis X9 via a motor (3) and a transmission mechanism.

In FIGS. 5 and 6, the massaging head (7) has three massaging tips (45, 46, 47) propelled to spin around Axes X10, X11 and X12 by a gear mechanism (48). These massaging tips (45, 46, 47) are at an incline with respect to the application surface (52).

In FIGS. 12 and 13, the massaging head (8) has two claws (49, 50) that extend toward the exterior of the application surface (51). These claws (49, 50) are flexible. The massaging head (8) has a rigid piece (53) with a chamber (54) into which the claws (49, 50) can enter, as they bend due to their flexibility, and close up. The lateral movement of the claws (49, 50) inside the chamber (54) is initiated by a traction mechanism in the direction of Arrow 55. The flexibility of the claws (49, 50) allows them to return to a spread-apart position when the traction mechanism allows these claws (49, 50) to move in the opposite direction of Arrow 55.

In one variant depicted in FIG. 7, the massaging appliance (1) has a crown (56) that may be positioned with the massaging heads (5, 6, 7, 8) with tips or claws. In FIG. 7, tips (58) are represented. This crown (56) is propelled to spin around Axis X13 and extends with respect to the application surface (57) such that the ends of the massaging tips (58) are positioned in the same plane as the outer edge (59) of the crown (56). This crown (56) is preferably activated to spin in an alternating movement around Axis X13 in the direction of Arrow 60. To do so, the massaging appliance (1) has a transmission mechanism (61) depicted in FIGS. 9 and 10. This transmission mechanism (61) has a gearbox (62) that is positioned in the body (2) of the massaging appliance (1). This gearbox (62) may be different from or the same as the gearbox of the motor (3). It can also be propelled by the same motor (3) via a gear system (not depicted), or even by a separate motor positioned in the body (2). An eccentric (63) is positioned on the shaft (64) of the gearbox (62). This eccentric (63) has a finger (65) that is offset from the spinning axis (X14) of the shaft (64). This finger (65) is positioned in a groove (66) located in a rack (67) rising laterally along Axis X15 and engaging with a pinion (68) which, in turn, engages with the crown (56), as depicted in FIGS. 9 and 10. Thus, the finger (65) has a certain degree of freedom inside the groove (66) when spinning around Axis X14, which transmits an alternating movement along Arrow 69 to the rack, and therefore an alternating spinning movement along Arrow 70 to the pinion (68) and to the crown (56). The advantage of this transmission mechanism (61) is to be able to easily change the angle of incline between the finger (65) and the groove (66), which makes it possible to attach the massaging head to the body (2) with different angular orientations, for example along the axis of the body (2) or at a 45° incline with respect to the body (2). One thus obtains a means of connection that is independent of the angles between the massaging head and the body. Such a connection can be used with variants of the transmission mechanism between the massaging head and the body, as necessary. One could also consider connection variants that are independent of the angle of incline between the massaging head and the body, such as, for example, a gear system with a conical or equivalent wheel.

In one variant depicted in FIG. 28, the massaging appliance (1) has a soft skin (71) on top of the application surface (72) of the massaging head (76) that covers the massaging tips (73, 74, 75). This soft skin (71) prevents the tips from feeling too aggressive and improves adhesion to the skin through surface contact. One can consider this soft skin with the claws (49, 50) in FIGS. 12 and 13 or the different variants with tips, or even other variants.

In one variant depicted in FIGS. 21 and 22, there is, on the massaging appliance (1), a cosmetic product dispensing system (77) that includes a flexible product reservoir (78) on which pressure is exerted by a small bar (79) that moves laterally in the direction of Arrow 80 along the length of the product reservoir (78). An activation system (81) moves the bar (79) along Arrow 80. This activation system (81) is, for example, comprised of a button (82) attached to the bar (79), which moves laterally in the direction of Arrow 80 when manually activated. A notched piece (83) holds a notch (84) on the button (82) whenever it is pressed, to hold the bar (79) in position, as it advances along the product reservoir (78). The dispensing system (77) includes a tube (85) the positioning of which allows it to dispense the cosmetic product onto the application surface (86), either between the massaging elements (87, 88), or through the massaging elements (87, 88), as depicted in FIG. 28. These massaging elements (87, 88) are massaging rollers in FIG. 28; but of course, these could be tips or claws. We see in FIG. 28 that the tube (85) has a first portion (85a) located in the body (2) of the massaging appliance, and a second portion (85b) located in the massaging head (89). An airtight means of connection (90) is established between the first portion (85a) and the second portion (85b) of the tube. Various methods of airtight connection (90) could be considered, such as a male-female connection equipped with airtight joints.

Other variants of the cosmetic product dispensing system can be considered. For example, one could consider an automatic activation system that continually and regularly dispenses the cosmetic product by means of a pump, such as an electric pump. One could also consider a system of dispensing the cosmetic product in a natural way, being dispensed regularly through physical phenomena that do not require external activation.

In one variant depicted in FIGS. 23 and 24, the dispensing system (91) includes a reservoir (92) that is flexible, and an actuator (93) that includes a lever (94) and a motorized finger (95) configured to move in an alternating motion as indicated by the arrows (96). The dispensing system (91) includes a sliding system (97) with an aperture (98) into which the back end (94a) of the lever (94) can move. The lever (94) is configured to be placed into a first position illustrated in FIG. 23, according to which the back end (94a) of the lever (94) is positioned behind (98a) the aperture, and said lever (94) is disengaged from the motorized finger (95). Thus, it is necessary to exert a manual force on the lever (94) to press on the reservoir (92) and dispense the cosmetic product through the tube (99), which may be configured similarly to the tube (85) in FIG. 28. On the other hand, when the back end (94a) of the lever (94) is positioned in front (98b) of the aperture, as illustrated in FIG. 24, the motorized finger (95) automatically activates the lever (94), which presses the reservoir (92) and dispenses the cosmetic product through the tube (99). Implementation variants of a cosmetic product dispensing system, with a system for switching to manual mode or automatic mode, could be considered while still remaining within the scope of the invention.

As depicted in FIG. 25, the massaging appliance (1) has a shaft (100) that is propelled to spin around Axis X16 by the motor (3), by means of a gear system (101) that is known to an expert in the field. The end (100a) of this shaft (100) is located in the massaging head (4, 5, 6, 7, 8, ta, bi, ja), for example on the casing (102), on the massaging elements, and receives a balance weight (103) that spins out of balance around Axis X16 and makes the massaging head vibrate while the massaging appliance (1) is being applied. Other variants of the vibration system can also be considered. In particular, one could consider positioning the balance weight (103) directly in the body (2) near the massaging head, to simplify the design and avoid having an additional connection system on the shaft (100) at the attachment point between the body and the massaging head. One could also consider completely integrating the vibration system inside the massaging head, in which a drive shaft activated by the motor (3) or another motor, penetrates the head, in which case a comparable attachment system to the one depicted in FIGS. 9 and 10 could then be considered, for example.

In one variant depicted in FIGS. 11 and 26, the massaging appliance (1) has, on the application surface (104) on the massaging head (105), light diodes (106) that are controlled by an electronic casing (not depicted) located inside the body (2). These light diodes (106) may be turned on, either automatically when the massaging head (4, 5, 6, 7, 8, ta, bi, ja) is activated, or separately by means of the distinct control button (not depicted). The light diodes (106) will be positioned, for example, on the outer edge (107) of the application surface (104), or even distributed over said application surface (104) outside the trajectories of the massaging elements. Light diodes of different colors or multi-colored diodes could be used, depending on the desired wavelength and/or treatment sought, or even a control unit that could be used to change the wavelength of these light diodes (106). A light transmission system (108) is positioned between the massaging head (4, 5, 6, 7, 8, ta, bi, ja) and the body (2). This light transmission system includes a fiber optic connection (109, 110) that directs the light emitted toward the application surface (104) or on the massaging elements, such as massaging tips.

In one variant of implementation depicted in FIG. 27, the massaging appliance (1) has two electrodes (111, 112) with different electric potential. These electrodes (111, 112) may consist of two massaging elements (113, 114) or they can be located on the application surface (115). These electrodes (111, 112) are powered by an electricity source (116) located in the body (2). This design makes it possible to perform a transcutaneous iontophoresis treatment before or during the application of a cosmetic product to the skin, thereby accelerating the penetration of the cosmetic product. This cosmetic product may be dispensed in a natural manner, manually or automatically, by the massaging appliance (1), or even applied directly to the skin by the user. The massaging appliance (1) has a removable means of attachment (117, 118) that is used to quickly connect or disconnect the electrodes (111, 112) when the massaging head (120) is attached to or detached from the body (2). For example, one could consider electrical contacts in the attachment area (121) between the massaging head (120) and the body (2).

As depicted in FIGS. 1 and 4, the massaging appliance (1) has a means of attachment (9) configured so that the massaging head (4, 5, 6, 7, 8, ta, bi, ja) can be attached to or detached from the body (2) quickly. This means of attachment (9) is implemented by means of a removable fastening system between the massaging head and the body. In the method of implementation in FIG. 4, the body (2) has slots (122, 123), and the massaging head (4, 5, 6, 7, 8, ta, bi, ja) includes a piece (124) that receives the mechanism (125) that transmits the movement to the massaging elements, connected to the motor (3) via an attachment system that is independent of the angle of incline of the massaging head with respect to the body (2). This piece (124) has notches (126, 127) and a means of retraction (128, 129) from the notches (126, 127) allowing them to retract for their positioning in the slots (122, 123), as well as their withdrawal from these slots (122, 123).

Different locking systems or means of retraction are illustrated in FIGS. 29 to 36 and keep a massaging head (130) attached to the body (2). In FIG. 29, a stopping system (131) using a ball (132) is depicted, and the ball (132) is attached to a spring (133) and is inserted into the groove (134) on the massaging head (130). In FIG. 30, a bayonet system (135) is depicted. In FIGS. 31 and 32, a valve and spring system (136) is depicted that locks a piece (137) secured to the massaging head. In FIGS. 33 and 34, a locking system (138) with a notch (139) and release latch (140) is illustrated in a locked and unlocked position of a piece (141). In FIGS. 35 and 36, a locking system (142) allows two notches (143, 144) to lock and unlock a piece (145). These different implementation variants are not limiting.

As depicted in FIGS. 14 to 20, the massaging appliance (1) has a means (146) of distinguishing the massaging head (147) attached to the body (2).

In FIGS. 14 and 15, the massaging head (146) has a circular-shaped protuberance (148) that is intended to be inserted into a circular groove (149) on the body (2). The body (2) includes a second circular groove (150). Mechanical contacts (151, 152) are placed in these circular grooves (149, 150). When the massaging head (146) is attached to the body (2), the protuberance (148) activates the mechanical contact (151). We see in FIG. 37 four massaging heads (153, 154, 155, 156) that can be attached to the body (2). The first massaging head (153) has no protuberance. The second massaging head (154) has one protuberance (157). The third massaging head (155) has two protuberances (157, 158). And the fourth massaging head (156) has one protuberance (158). When these massaging heads (153, 154, 155, 156) are attached to the body (2), they activate either one or both of the two mechanical contacts (159, 160), which is how they are distinguished based on the binary code programmed into the control unit (161) depicted in FIG. 14. This control unit (161) is configured to control the various actuators in the massaging appliance (1) based on the type of massaging head attached. Thus, for example, the control unit (161) controls the activation of the motors, cosmetic product dispensing pumps, the transcutaneous iontophoresis treatment device, the vibration system, the light system, etc.

In FIG. 16, we see that the protuberances (162, 163) are positioned on the body (2) and implemented by the mechanical contacts (164, 165). Whereas, the massaging head (147) has a circular groove (166).

Variants can be considered within the scope of the invention. In particular, the mechanical contacts could be replaced with magnetic contacts or sensors.

In FIGS. 14 and 17 to 20, optical sensors (167) are depicted. In FIG. 17, the massaging head (147) has a transparent surface (168) that allows the light emitted by a light diode (169) to pass through, to be detected by the optical sensor (170). Thus, the light is detected by transparency. In the variant in FIG. 18, the surface (171) is opaque, and the sensor (170) therefore detects opacity when the massaging head (147) is attached. In FIG. 19, a separator (172) is positioned between the massaging head (147) and the body (2). In FIG. 20, a mirror system is placed between the massaging head (147) and the body (2).

Other variants can be considered while still remaining within the scope of the invention, particularly with regard to distinguishing the massaging heads on the body (2) and the control unit (161). For example, the sensors may be used to detect that the massaging head (147) is properly attached to the body (2).

Figure 38:
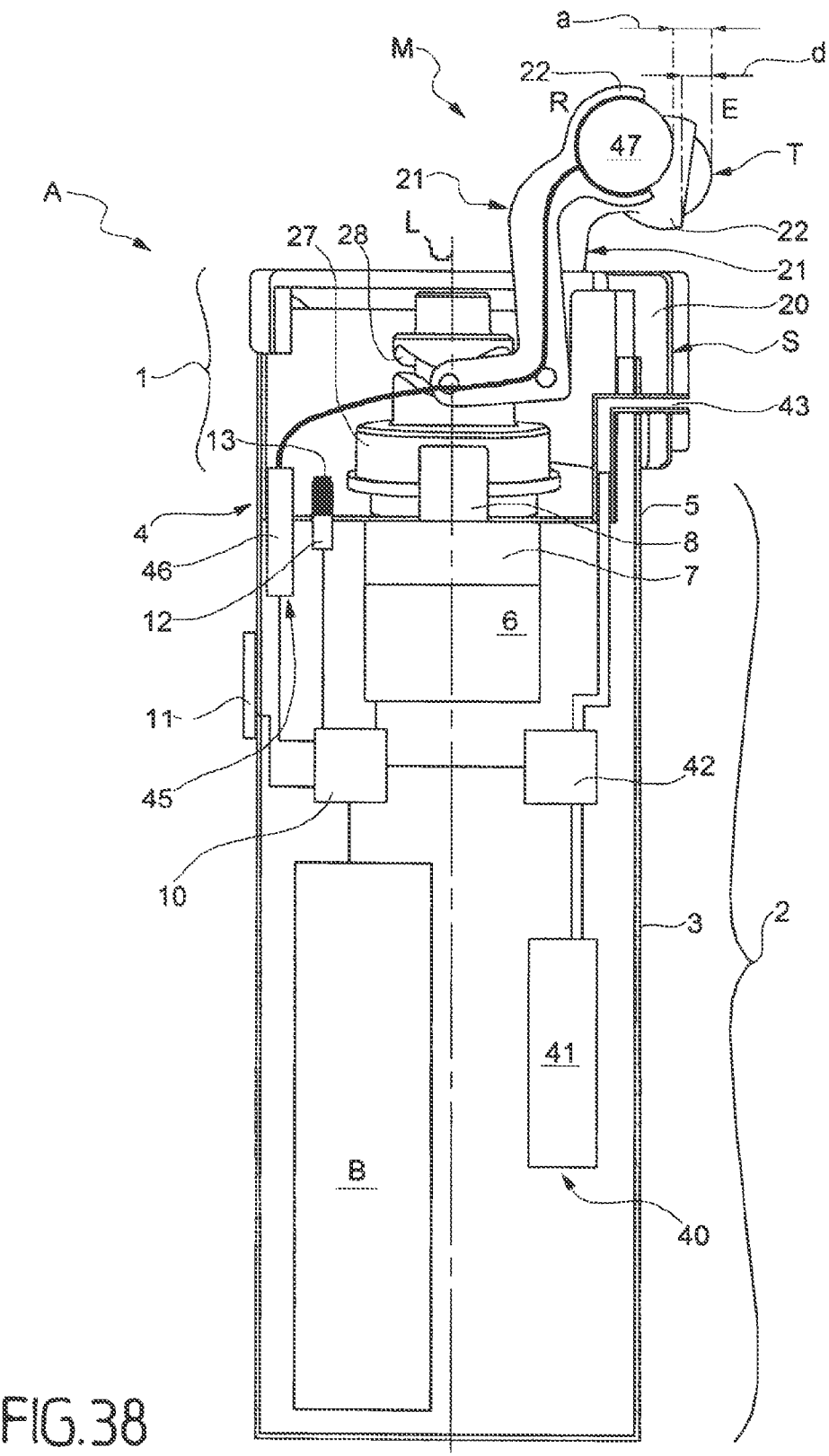
FIGS. 38 to 44 depict a head described in the invention, referred to as a "tapping head," and have their own reference numbers.

With Regard to the "Tapping Head" Depicted in FIGS. 38 to 44, with its Own Reference Numbers:

A massaging appliance described in the invention, as depicted in FIG. 38 and designated overall by Reference A, consists of a massaging head (1), designed to be removable, on a drive unit (2). The massaging head (1) is designed to exert a mechanical action on the skin of the user's face via massaging elements (M) propelled by an electric motor.

To this end, the drive unit (2) consists of an elongated body (3) in a generally cylindrical shape that has, at one of its ends (4), a removable means of adaptation (5) of the massaging head (1). In the example depicted, the means of adaptation (5) is formed by a sheath, inside of which the massaging head (1) is partially inserted.

Inside the body (3), the drive unit (2) has an electric motor (6) that activates a driving means (7) designed to transmit the movement of the electric motor to the massaging elements of the massaging head (1). In the example illustrated, the driving means (7) includes a reduction gear, not depicted, that drives an output shaft (8) that is accessible at the point of the adaptation means (5) of the drive unit (2).

The electric motor (6) is operated by a control unit (10) powered by a battery pack (B) positioned inside the body (3). Of course, the electrical power to the control unit (10) could also be provided directly from the power grid via a transformer. The control unit (10) is also connected to a manual control interface (11) that is accessible from the exterior of the body (3). The manual control interface (11) may, for example, include a stop/start switch and/or a means of manually selecting the operating programs.

The drive unit (2) also has a distinguishing means (12) that is connected to the control unit (10) and is adapted to read the means of identification (13) on the massaging head (1). The control unit (10) is thus adapted to control the operation of the massaging appliance (A) depending on the massaging head (1) as distinguished after the identification means (13) is read. Functional control of the massaging appliance (A) may consist, in particular, of determining the rotation speed of the electric motor (6) so that it is appropriate for the massage that is to be performed by the massaging elements (M). The means of identification (13) may, for example, consist of a RFID chip, while the distinguishing means (12) will be designed to read such a RFID chip. Of course, the identification means (13) and the distinguishing means (12) may be implemented in any other appropriate manner, such as, for example, in the form of an identification system based on mechanical or electrical contact, or even in the form of a magnetic identification system using permanent magnets and reed switches.

Figure 39:
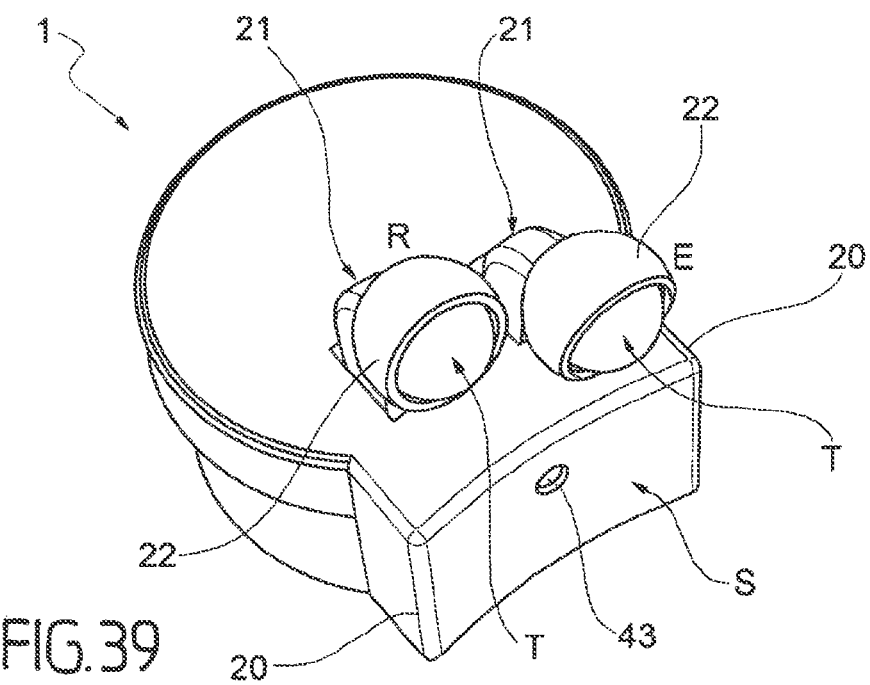

In the invention, the massaging head (1) is designed to perform a tapping massage. To this end, the massaging head (1) includes, as shown in FIG. 39, a pressure element (20) that is intended to press against the face to define a working distance. Thus, the pressure element (20) defines a pressure surface (S) that forms a reference surface.

In the example depicted, the pressure surface (S) is smooth and is in a concave shape that allows it to conform to the cheekbones when the massage is being performed under or around the eyes.

The massaging head (1) has, above the pressure surface (S) and opposite the drive unit (2) with respect to said pressure surface (S), the massaging elements (M), which have at least two massaging fingers (21), each with a work head (22) that is intended to come in contact with the face.

The two massaging fingers (21) each move between, on the one hand, a position of retraction (R) corresponding to the position of the massaging finger (21) located in the forward position in FIG. 39 and, on the other hand, a position of extension (E) corresponding to the position of the massaging finger (21) located further back in FIG. 39.

In a position of retraction (R), the work head (22) of each massaging finger (21) is located below the pressure surface (S) toward the interior of the massaging head (1). Whereas, in a position of extension (E), the work head (22) of each massaging finger (21) is located above the pressure surface (S) toward the exterior of the massaging head (1). Each work head (22) thus has, between its positions of retraction (R) and extension (E), a movement amplitude of between 5 mm and 15 mm. Moreover, in a position of extension (E), each work head (22) protrudes from the pressure surface (S) by a distance ranging from 2 mm to 10 mm.

The massaging head (1) also has a maneuvering means (25) designed to move each of the massaging fingers (21) in alternation between its positions of extension (E) and retraction (R). The maneuvering means (25) are thus designed to cooperate with the driving means (7), and more specifically with the output shaft (8) so as to transmit and transform the rotation movement of the electric motor (6) into an alternating movement of the massaging fingers (21).

In the example illustrated, each massaging finger (21) is generally in the shape of an S and is carried on a joint pin (26) located in the lower part of the corresponding massaging finger (21), while the upper portion of said massaging finger (21) carries the work head (22). The maneuvering means thus include a cam (27) than spins on itself in a direction that is perpendicular to the joint pin (26) and coaxial to the output shaft (8). Thus, on a lower surface, the cam (27) has a housing to receive the output shaft (8). The cam (27) also includes a peripheral cam channel (28), the shape of which is roughly sinusoidal. Each massaging finger has, at a distance from the joint pin (26), a lug (29) inserted into the cam channel (28) such that the rotation of the cam (27) on itself causes an alternating movement of each lug (29). In light of the conformation of the massaging fingers (21), the alternating movement of each lug (29) causes an alternating oscillation of the massaging fingers rotating around the joint pin (26).

Preferably, the massaging appliance (A), and more particularly, the maneuvering means (25), the driving means (7), and the control unit (10) are designed to give each of the massaging fingers a movement frequency of greater than or equal to 2.5 Hz.

It should be noted that, in the example depicted, the maneuvering means (25) is designed to coordinate the movement of the massaging fingers (21) such that when one of the massaging fingers (21) is in a position of extension (E), the other massaging finger (21) is in a position of retraction (R) and vice versa.

The massaging appliance thus constructed is implemented as follows. The pressure surface (S) is placed against the face, and then the user turns on the massaging appliance (A) using the interface (11). The massaging fingers (21) then begin to move in oscillation, which imitates the act of massage that would be performed using two fingers, such as the index and middle fingers alternately tapping the skin of the face, and particularly the skin around the eyes.

In the example depicted, and in order to simulate as closely as possible the actions of the fingers, each work head has a work surface (T) with a convex shape, and in this case with a spherical, rigid shape.

Figure 40:
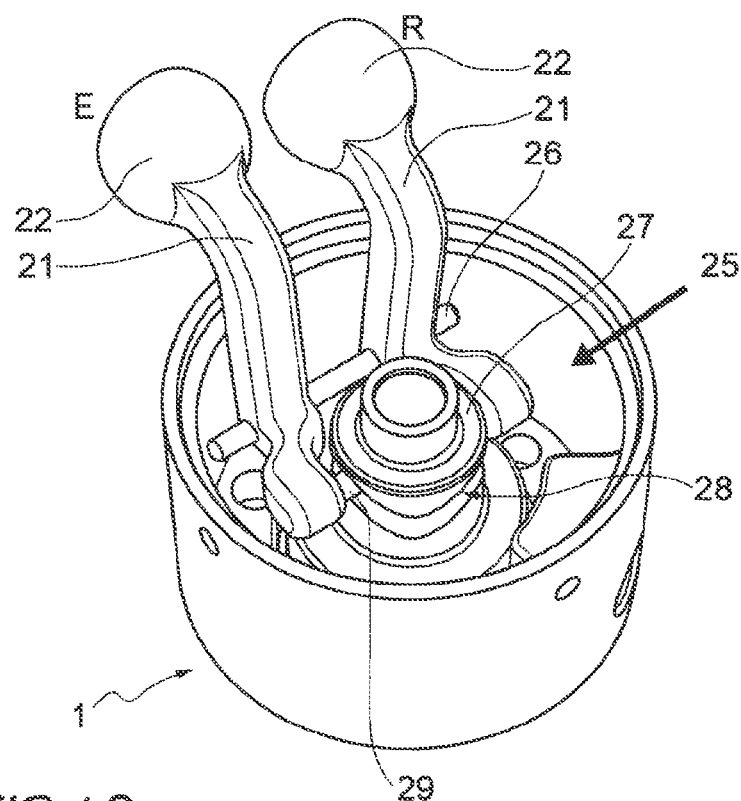

Massages performed using the appliance described in the invention produce stimulating, smoothing and relaxing effects, thereby reducing circles or bags under the eyes, and filling in wrinkles and fine lines. In order to optimize this treatment, the massaging appliance (A) as depicted in FIGS. 38 to 40 includes a means (40) of applying or dispensing a cosmetic product. In the example depicted, the means of applying a cosmetic product (40) consists of a reservoir (41) located in the drive unit (2) and connected, via a sampling system (42), for example a sampling pump (42), to a dispensing nozzle (43) located in the pressure element (20). The sampling pump is operated by the control unit (10) such that it dispenses the cosmetic product when the massaging appliance (A) is operating. Of course, one of the work heads, or even both work heads, may include a cosmetic product dispensing nozzle.

Moreover, once again in the example depicted in FIGS. 38 to 40, the massaging appliance (A) also has a means of applying an electrical current to the skin (45), which includes a unit (46) to generate an electrical current and/or voltage. The generator unit (46) is operated by the control unit (10). The generator unit (46) is connected to an electrode (47) carried on a work head (22).

When the massaging unit (A) is in use, the control unit (10) operates the generator unit (46) such that when the electrode (47) is in contact with the skin, an electrophoresis phenomenon is created, which promotes the assimilation of the active principles of the cosmetic product.

Figure 41:
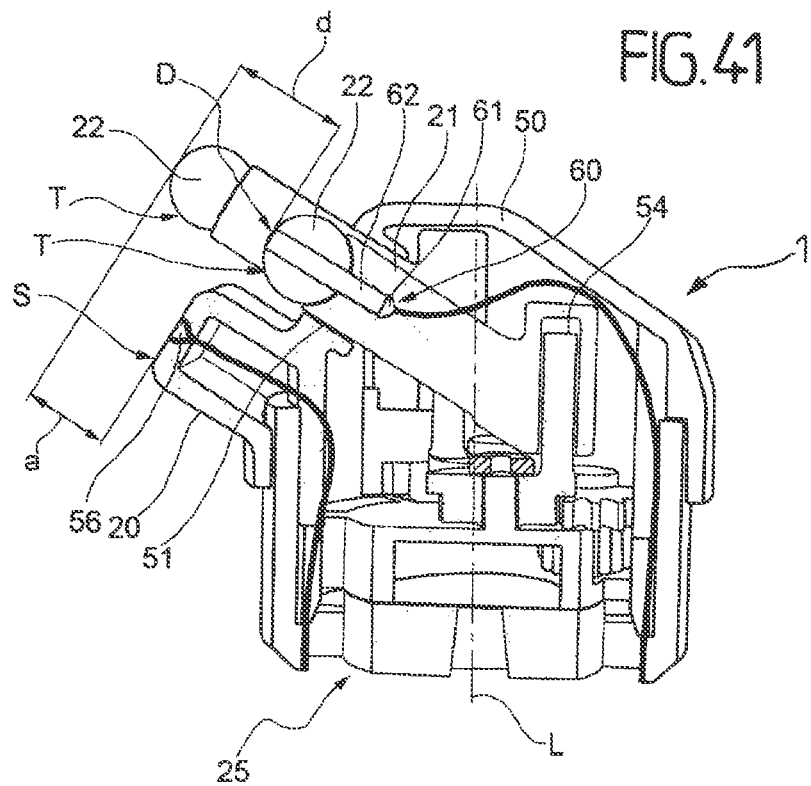
Figure 42:
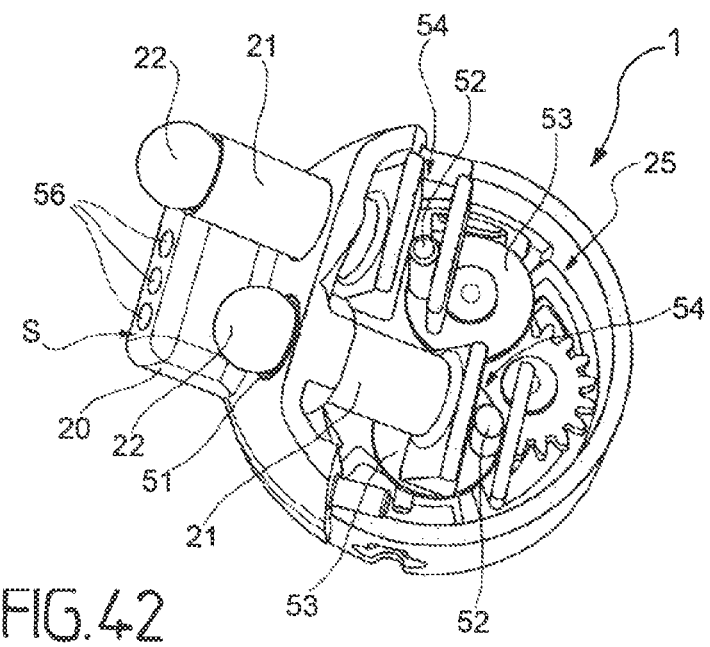

In the invention, the massaging fingers (21) are not necessarily propelled in an oscillating movement around a horizontal axis. Thus, FIGS. 41 and 42 show a massaging head (1) for an appliance described in the invention, in which the massaging fingers (21) have different kinematics.

In this example, each massaging finger (21) is constructed in the shape of a sort of rectilinear piston that extends at least partially to the exterior of a hollow body (50) surrounding the maneuvering means (25). Each finger is then guided laterally by a bore (51) placed in the hollow body (50). The end of each massaging finger (21) located inside the hollow body (50) cooperates with an off-center pin (52) carried on a maneuvering disc (53) belonging to the maneuvering means (25). The off-center pin (52) is positioned in a chamber (54) that is connected rigidly to the corresponding massaging finger, and in which the off-center pin (52) can move laterally, such that its rotation with the maneuvering disc (53) is transformed into a lateral movement of the corresponding massaging finger (21).

In addition, in this example of implementation, the pressure surface (S) is flat.

Still in this example of implementation, the clearance or course of the massaging fingers is not perpendicular to the longitudinal axis (L) of the drive unit, but forms a non-zero angle with it, and in the example illustrated, an angle of approximately 30°. This method of implementation offers the advantage of allowing the user to reach the narrow areas of the face more easily, such as the outline of the eyes or mouth, without being encumbered by the body of the appliance.

Moreover, in this example of implementation, the pressure element (20) has electrodes (56) for transmitting an electrical current to the skin.

Still in this example of implementation, the massaging head has a means (60) of diffusing light in the direction of the face. In this case, the diffusion means (60) is located in a massaging finger (21) and includes a light source (61) such as an electroluminescent diode operated by the control unit (10). The light source (61) is then paired with an optical system (62) with an output panel (D) located on the work surface (T) and therefore intended to be pointed toward the face of the person using the massaging appliance (A) described in the invention.

Figure 43:
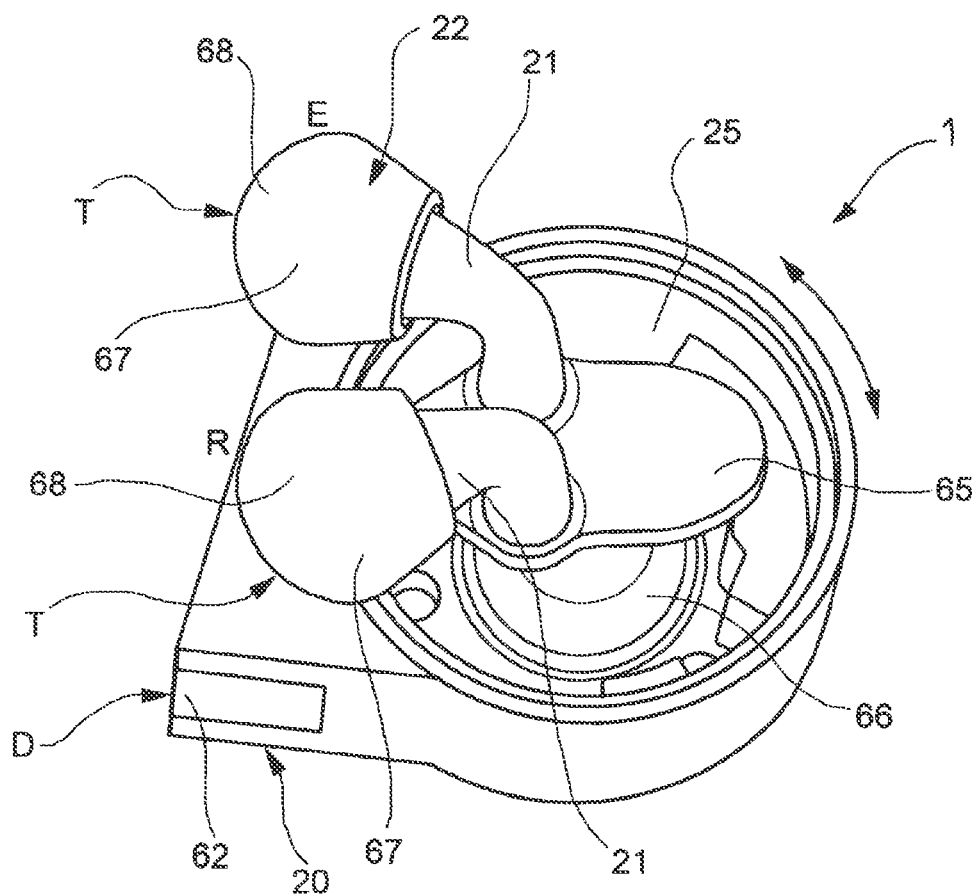

FIG. 43 further illustrates another implementation variant of a massaging head (1) of a massaging appliance (A) described in the invention. In this variant, the two massaging fingers (21) are carried on a single plate (65) that oscillates in rotation around a vertical axis while being propelled, via a bore beneath the plate, by an off-center disc (66) belonging to the maneuvering means (25) and in which the pin is positioned in the bore of the plate. In this example of implementation, each massaging finger (21) has a removable cap (67) that forms the corresponding work head (22).

In another example of implementation, this cap may be made of a soft elastomer-type material.

In another method of implementation, it may include a pad (68) soaked in a cosmetic product forming the work surface (T). The removable caps (67) thus form the means of applying or dispensing a cosmetic product.

In this example of implementation, the pressure element (20) includes an optical system (62) for diffusing the light produced by a source located either in the massaging head (1) or in the drive unit (2).

Figure 44:
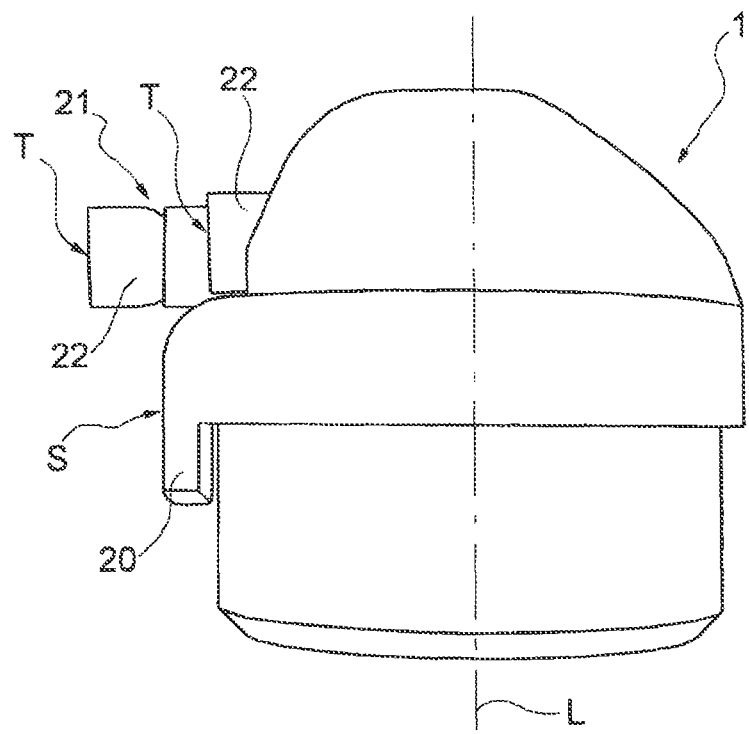

FIG. 44 depicts an implementation variant of the massaging head depicted in FIGS. 41 and 42, of which it shares the maneuvering kinematics of the massaging fingers (21). This implementation variant differs from the massaging head depicted in FIGS. 41 and 42 in that the massaging fingers move laterally in alternation in a direction perpendicular to the longitudinal axis (L) of the drive unit. In addition, in this form of implementation, the work surface (T) of each massaging finger is flat.

With Regard to the "Interior Work Zone" Head Depicted in FIGS. 45 to 49, with its Own Reference Numbers:

It should be noted that in these drawings, the structural and/or functional elements common to the different variants may have the same reference numbers.

Figure 45:
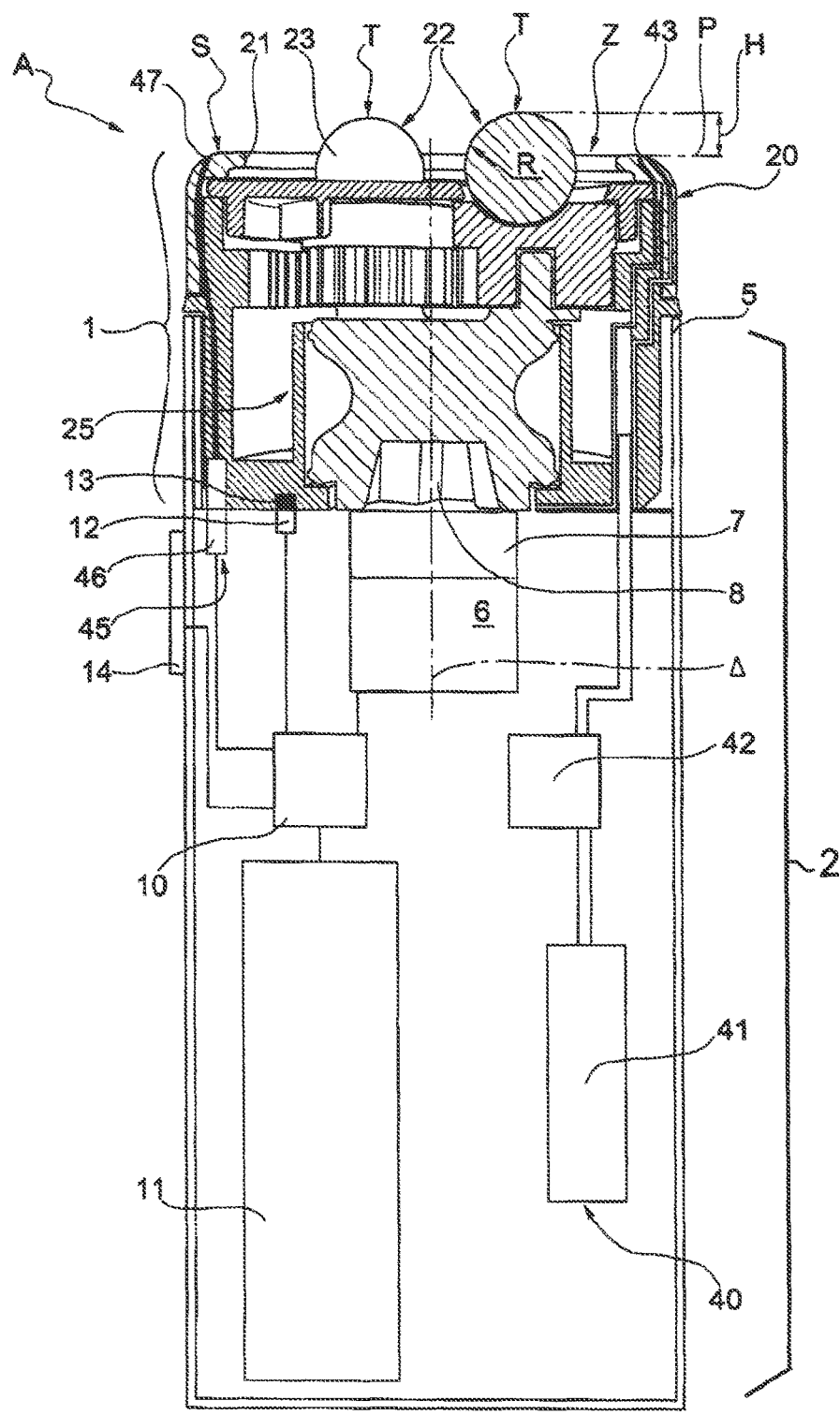
FIGS. 45 to 49 depict a head described in the invention known as an "interior work zone head" and have their own reference numbers.

A massaging appliance described in the invention, as depicted in FIG. 45 and designated on the whole by Reference A, consists of a massaging head (1), designed to be removable, on a drive unit (2). The massaging head (1) is designed to exert a mechanical force on the skin of the user's face via massaging elements that are propelled by an electric motor.

To this end, the drive unit (2) has an elongated body that is generally in a cylindrical shape, which has on one of its ends a means of attaching (5) the massaging head (1), in a removable manner. In the example illustrated, the means of attachment (5) is formed by a sheath inside of which the massaging head (1) is partially inserted.

The drive unit (2) has, inside the body (3), an electric motor (6) that activates a driving means (7) designed to transmit the movement of the electric motor to the massaging elements of the massaging head (1). In the example illustrated, the driving means (7) has a reduction gear, not depicted, that drives an output shaft (8) that is accessible at the attachment means (5) of the drive unit (2).

The electric motor (6) is operated by a control unit (10) powered by a battery pack (11) placed inside the body. Of course, the electrical power of the control unit (10) could also come directly from the power grid through a transformer. The control unit (10) is also connected to a manual control interface (14) accessible from the exterior of the body. The manual control interface (14) can, for example, include a start/stop switch and/or a means of manually selecting the operating programs.

The drive unit (2) also contains a distinguishing means (12) that is connected to the control unit (10) and is designed to read the identification means (13) on the massaging head (1). The control unit (10) is thus designed to control the operation of the massaging appliance (A) depending on the massaging head (1) as distinguished upon reading the identification means (13). The operational controls of the massaging appliance (A) can consist of a setting for the rotation speed of the electric motor (6) so that it is appropriate for the massaging that is to be performed by the massaging elements. The identification means (13) may, for example, consist of a RFID chip, while the distinguishing means (12) will be designed to read such a RFID chip. Of course, the identification means (13) and distinguishing means (12) may be made in any other appropriate manner, such as, for example, in the form of an identification system via mechanical or electrical contact, or even in the form of a magnetic identification system using permanent magnets and reed switches.

Figure 46:
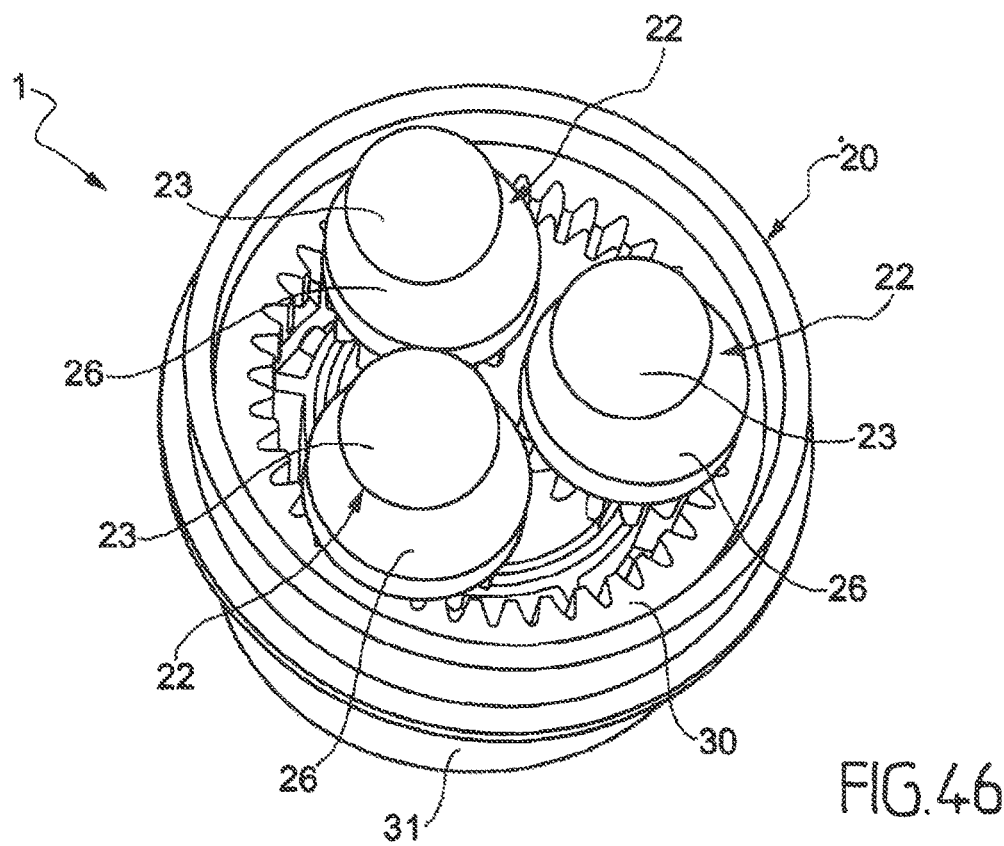

In the invention, the massaging head (1) is designed to perform a massage by moving a work head against the skin, while the head remains in constant contact with the skin. To this end, the massaging head (1) includes, as shown in FIG. 46, a pressure element (20) that is intended to come into contact with the face. The pressure element (20) is generally ring-shaped and forms a pressure crown (21) that defines a pressure surface (S) within a pressure plane (P), said pressure surface (S) being designed to be able to fully conform to the skin if the user so desires. In the example illustrated, the pressure element (20) is hollow and rigid, while the pressure surface (S) is formed by an elastically bendable material such as an elastomer (for example silicone or EPDM). Thus, the pressure surface (S) can be bent a few millimeters, and preferably at least two, in order to conform to the shape of the area of the face against which it is applied.

The pressure crown (21) outlines a work zone (Z) inside of which there is at least, in the example illustrated, three work heads (22), each with a work surface (T) extending beyond the pressure plane (P). In the example illustrated, each work head (22) has a ball (23), such that the corresponding work surface (T) has a convex, and more specifically spherical, shape. Each work surface (T) thus extends permanently to protrude from the pressure plane (P) at a height (H), as measured between the summit of the work surface (T) and the pressure plane (P), of preferably greater than or equal to the curve radius (R) of said ball. In one variation, the height (H) of protrusion of each work surface (T) is greater than half the curve radius (R), but less than the curve radius (R).

In the example illustrated, each ball (23) belonging to a work head (22) is made of a rigid material such as metal. Thus, each work surface (T) is rigid, as opposed to the flexible or elastically bendable quality of the pressure surface (S). Moreover, in this example, the surface of each ball (23) is smooth.

In the invention, the massaging head (1) also has a maneuvering means (25) designed to spin each work head (22) along an axis (Δ) that is offset from the center of each corresponding work surface (T). The maneuvering means (25) is thus designed to cooperate with the driving means (7) and more specifically with the output shaft (8), so as to transmit and transform the rotation movement of the electric motor (6) into a spinning movement of the work heads (22).

Figure 47:
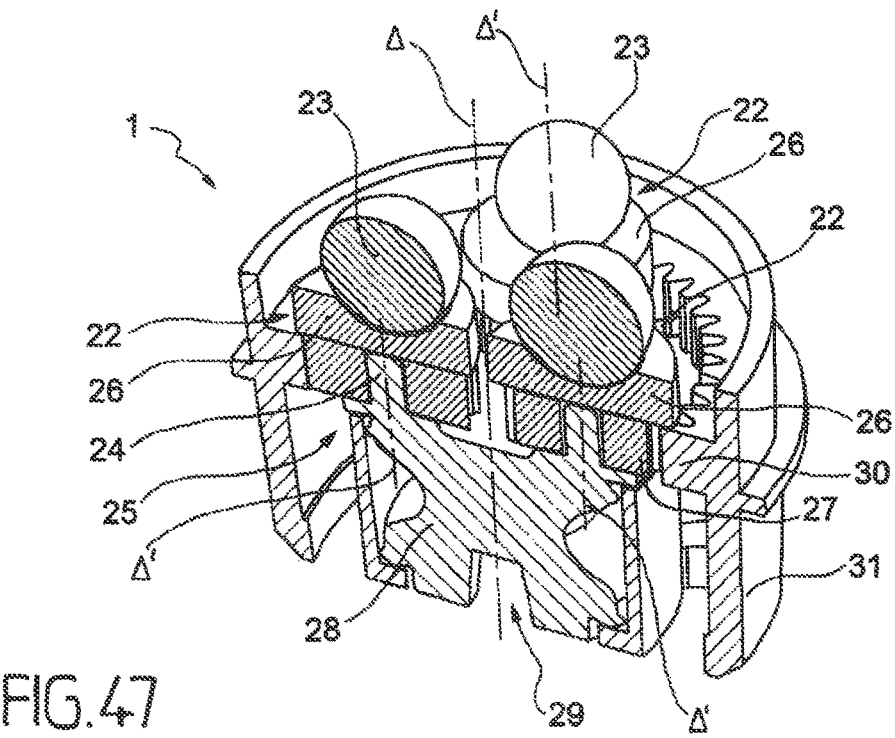

In the example illustrated, and as shown in FIGS. 46 and 47, the maneuvering means (25) are designed move the three balls (23) in a planetary motion, which is to say a main rotation movement of the three balls (23) around the axis of rotation (Δ), combined with a secondary rotation movement of each of the balls around a secondary rotation axis (Δ') while the massaging appliance described in the invention is operating.

To this end, each work head (22) has a disc (26) that is centered with respect to the secondary axis of rotation (Δ') and that carries on its upper surface the corresponding ball (23) connected in a rigid manner to said disc (26). Each work head also has a planetary pinion (27) that is connected in a rigid manner to the lower surface of the corresponding disc (26) and that is coaxial to the secondary axis of rotation (Δ').

The maneuvering means (25) thus includes a maneuvering shaft (28) with an axis (Δ) that has on its interior surface a housing (29) to receive the output shaft (8), and that carries on its upper surface three pinions (24), each engaged in an axial bore of a planetary pinion (27). The maneuvering means also includes a fixed peripheral crown (30) connected in rigid manner to a casing (31) that constitutes the massaging head (1). Each of the planetary pinions (27) engages with the fixed peripheral crown (30), such that the rotation of the maneuvering shaft (28) causes the planetary movement of the balls (23) described previously.

In this illustrated variant, one could switch the materials used for the balls and the pressure crown, which is to say, balls made of a flexible material and a crown made of a rigid material.

As necessary, and in order to attenuate the kneading, one could also construct the massaging head (1) such that each work head (22) is mounted on Axis Δ', such that it performs a regular rotation on itself.

The massaging appliance thus created is implemented as follows. The pressure surface (S) is placed against the face, and then the user turns on the massaging appliance (A) using the manual control interface (14). The work heads (22) then begin to move in a planetary rotation movement, while the skin around the work zone (Z) is held by the ring-shaped pressure surface (S).

The massage performed using the appliance described in the invention can deeply knead the skin of the face, thereby reducing wrinkles and stimulating blood circulation and initiating the production of the elements that make up the skin.

In order to optimize this treatment, the massaging appliance (A) as illustrated in FIG. 45, has a means (40) of applying a cosmetic product. In the example illustrated, the means of applying a cosmetic product (40) includes a reservoir (41) located in the drive unit (2) that is connected, via a sampling system (42) such as a pump, to a dispensing nozzle (43) located in the pressure element (20). The sampling pump (42) is operated by a control unit (10) so as to dispense a cosmetic product while the massaging appliance (A) is operating. Of course, the pressure element (20) could include more than one dispensing nozzle. In addition, each work head could also have a cosmetic product dispensing nozzle that would be supplied from a flexible reservoir located in the corresponding work head and activated by a cam system as said work head spins.

Moreover, still in the example illustrated in FIGS. 45 to 47, the massaging appliance (A) also has a means of applying an electrical current (45) that includes a unit (46) that generates an electrical current and/or voltage. The generator unit (46) is operated by the control unit (10). The generator unit (46) is connected to an electrode (47) carried on the pressure element (20).

When the massaging appliance (A) is in use, the control unit (10) operates the generator unit (46) such that when the electrode (47) is in contact with the skin, an electrophoresis phenomenon is induced, thereby promoting the assimilation of the active principles of the cosmetic product.

In the invention, the work heads (22) are not necessarily propelled in a planetary-type movement as previously described.

Figure 48:
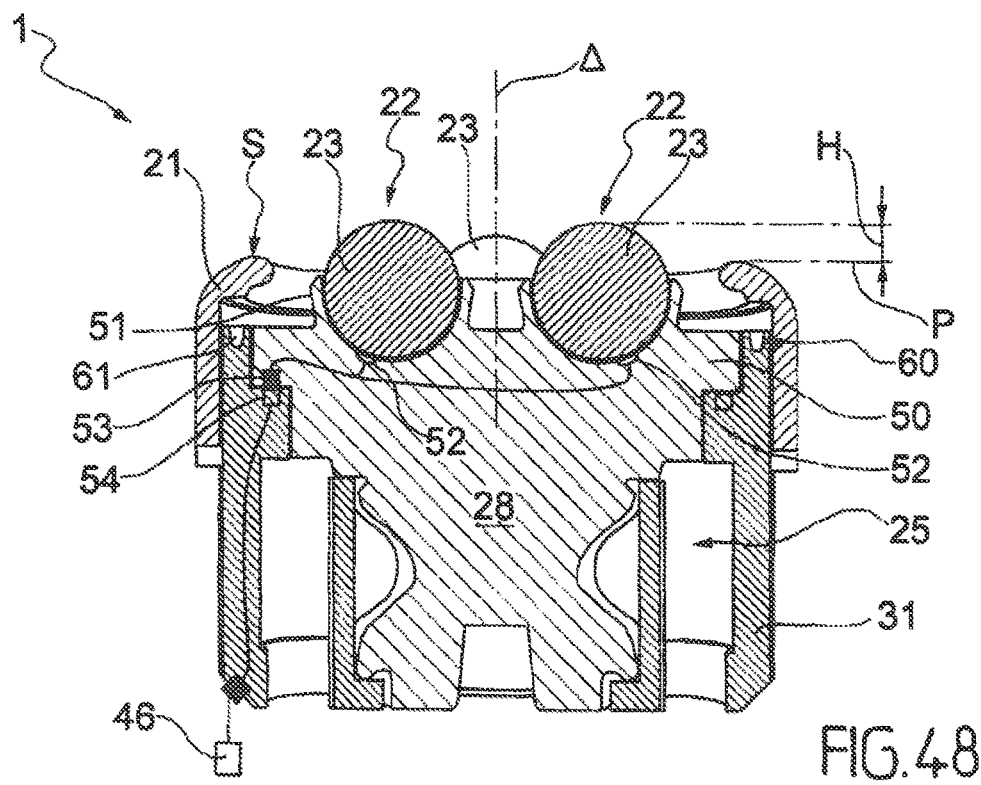
Figure 49:
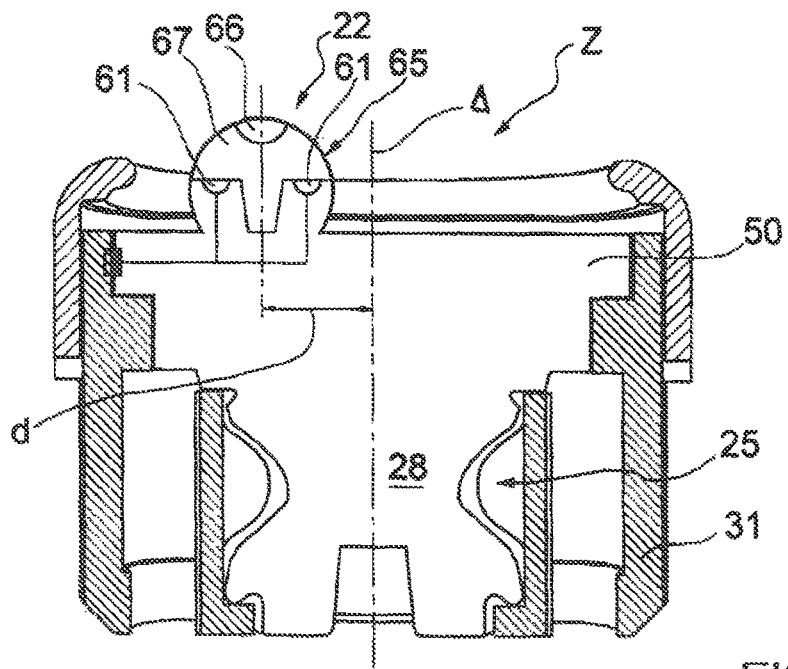

Thus, FIG. 48 illustrates one implementation variant of a massaging head for a massaging appliance described in the invention, which differs from the one described in reference to FIGS. 45 to 47, in that the three work heads (22) are carried on a circular plate (50) connected in rotation to the maneuvering shaft (28). The plate (50) carries the three work heads (22) formed by the metal balls (23), the centers of which are offset from the axis of rotation (A). Moreover, the balls (23) are each enclosed in a small hemispherical dish (51) that is connected rigidly to the plate (50). Thus, each ball (23) can spin on itself, such that it can roll over the skin while the massaging appliance described in this variant of implementation is in use.

In addition, in this example of implementation, each work head includes an electrostimulation electrode formed by the corresponding ball (23), which is connected electrically to the current generator unit (46) via a brush system (52, 53) and an annular channel (54).

Still in this example of implementation, the massaging head has a means (60) of diffusing light toward the face. In this case, the means of diffusion (60) is located in the massaging head and includes, as a light source, electroluminescent diodes (61) operated by the control unit (10). The sources of light (61) are then combined with an optical system formed by the pressure element, which is transparent, and which includes a light output surface located on the pressure surface (S) and therefore intended to be pointed toward the face of the person using the massaging appliance (A) described in the invention.

To this end, the entire work zone (Z) can be made of transparent pieces in order to allow light to pass through.

FIG. 48 depicts yet another implementation variant of a massaging head (1) of a massaging appliance (A) described in the invention. In this variant, the massaging head (1) has only one work head (22) in a spherical shape, which is connected in a rigid manner to the plate (50), but offset from its center. In this example of implementation, the center of the massaging head (22) is offset from the center of the work zone (Z), through which Axis Δ passes by a distance of greater than or equal to ⅙ of the smallest dimension of the work zone (Z), in this case the diameter of the work zone (Z), and less than half of said smallest dimension of the work zone (Z).

In this example of implementation, the work head (22) has a removable cap (65) that forms a corresponding work surface and has, on its summit, a pad (66) soaked in cosmetic product. The removable cap (65) thus forms a means of applying a cosmetic product.

In this example of implementation, the cap (65) also has an optical system (67) for diffusing the light produced by the light sources (61) located in the work head (22). The optical system (67) in this case is formed by a spherical cap made of a transparent material that functions as a light guide.

With Regard to the "Jacquet Pinching" Head Illustrated in FIGS. 50 to 56, with its Own Reference Numbers:

It should be noted that in these drawings, the structural and/or functional elements common to the different variants may have the same reference numbers.

Figure 50:
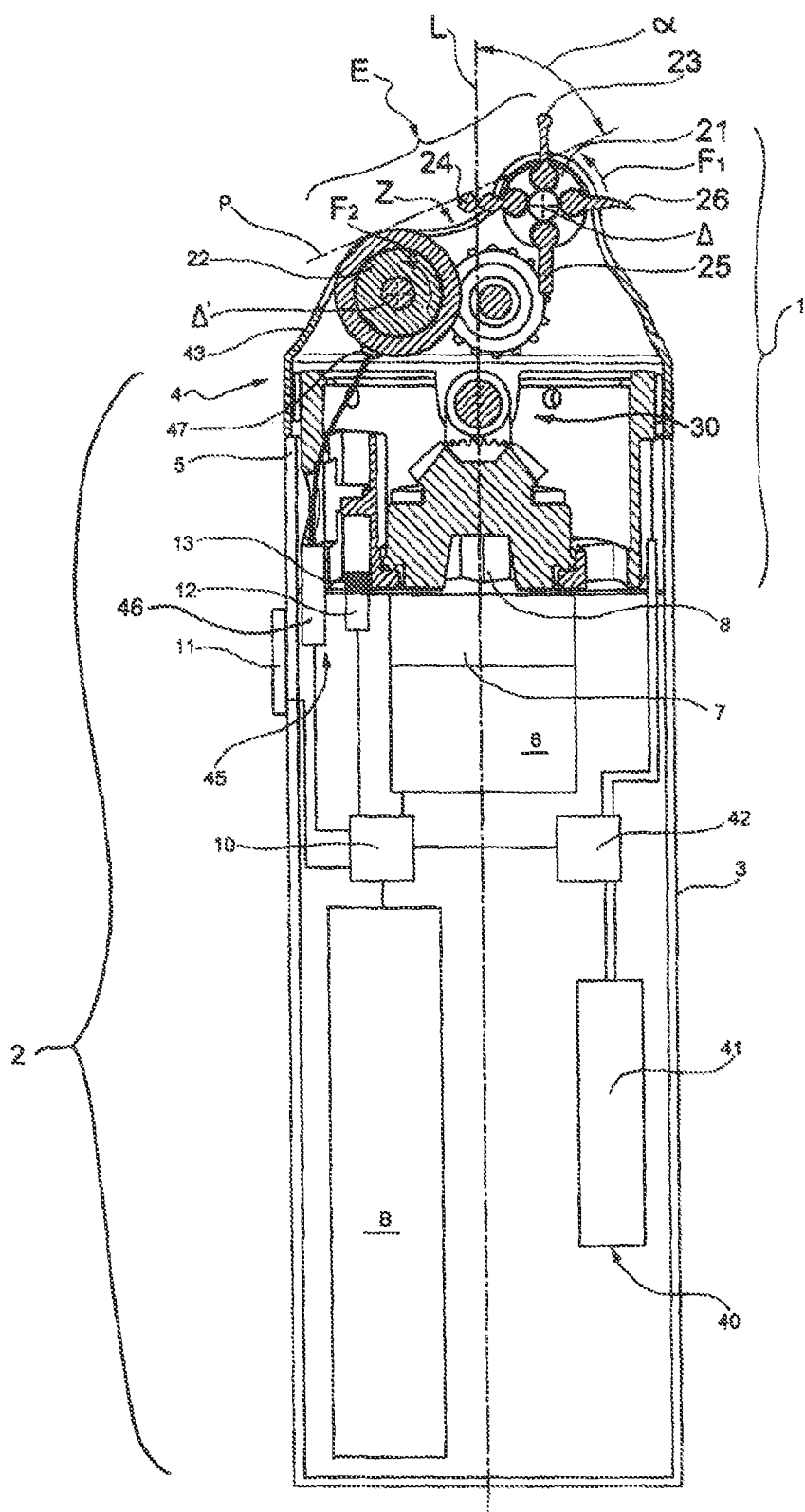
FIGS. 50 to 56 depict a head described in the invention known as a "Jacquet pinching head," and have their own reference numbers.

A massaging appliance described in the invention, as illustrated in FIG. 50 and designated on the whole by Reference A, consists of a massaging head (1) that is designed to be removable, on a drive unit (2). The massaging head (1) is designed to exert a mechanical action on the skin of a user's face, via massaging elements (E) that are propelled by an electric motor.

To this end, the drive unit (2) has an elongated body (3) with a generally cylindrical shape, that has on one of its ends (4) a removable means of adaptation (5) of the massaging head (1). The means of adaptation (5) is, in the example illustrated, formed by a sheath inside of which the massaging head (1) is partially inserted.

The drive unit (2) has, inside the body (3), an electric motor (6) that activates a driving means (7) designed to transmit the movement of the electric motor to the massaging elements of the massaging head (1). In the example illustrated, the driving means (7) include a reduction gear, not depicted, that drives an output shaft (8) that is accessible at the means of adaptation (5) of the drive unit (2).

The electric motor (6) is operated by a control unit (10), powered by a battery pack (B) located inside the body (3). Of course, the electrical power of the control unit (10) could also be provided directly from the power grid via a transformer. The control unit (10) is also connected to a manual control interface (11) that is accessible from the exterior of the body (3). The manual control interface (11) may, for example, have a stop/start switch and/or a means of manually selecting operating programs.

The drive unit (2) also has a distinguishing means (12) that is connected to the control unit (10) and that is designed to read a means of identification (13) on the massaging head (1). The control unit (10) is thus designed to control the operation of the massaging appliance (A) based on the massaging head (1) as distinguished upon reading the identification means (13). Controlling the operation of the massaging appliance (A) may consist of determining the rotation speed of the electric motor (6), such that it is appropriate for the massage to be performed by the massing elements (E). The means of identification (13) may, for example, consist of a RFID chip, while the distinguishing means (12) will be designed to read such a RFID chip. Of course, the identification means (13) and distinguishing means (12) may be made in any other appropriate manner, such as, for example, in the form of an identification system by mechanical or electrical contact, or even in the form of a magnetic identification system using permanent magnets and reed switches.

In the invention, the massaging head (1) is designed to perform a massage by pinching. To this end, the massaging head (1) has, as its massaging elements (E), two massaging rollers (21 and 22) that can spin on themselves along two spinning axes, Δ and Δ', which are parallel to one another and to an application surface (S) that is more clearly seen in FIG. 51. The two massaging rollers (21 and 22) are apart from one another, separated by a work zone (Z). In the example illustrated, the distance between the spinning axes Δ and Δ' is constant.

Moreover, in the example illustrated, the massaging rollers (21 and 22) are located inside the massaging head (1) such that a plane (P) tangent to the two rollers and located toward the exterior of the massaging head forms, with a longitudinal axis of the drive unit (2), a non-zero angle that is not a right angle.

In the invention, a first roller (21) has at least one paddle, and in this case, represented as an example, four paddles (23 to 27) that protrude radially from the surface of the first roller (21). The outer surface of the first roller (21) is retracted from the application surface (S). The paddles (23 to 27) extend radially far enough to protrude from the application surface (S) as the first roller (21) spins. The paddles (23 to 27) are also distributed regularly on the periphery of the first roller (21) and are, in this case, placed at 90° from one another.

Figure 56:
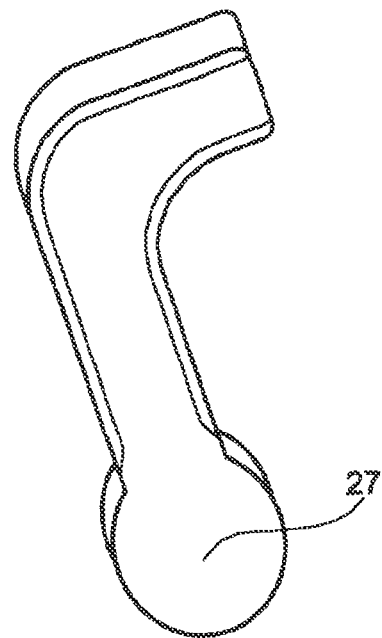

In the example illustrated, the paddles (23 to 27) have straight transversal sections that can be seen in FIGS. 50 and 56, of varying shapes, with the understanding that all the paddles could have the same shape. Thus, Paddle 23 has, when viewed as a straight transversal cross section, a free end that is thicker than the rest of the paddle (23). As for Paddle 24, when viewed as a straight transversal cross section, it is in a "figure 8" shape. Paddle 25, when viewed as a straight transversal cross section, has a straight shape. The straight transversal cross section of Paddle 26 has an elongated, slender shape that gets thinner toward the end. To better understand, this shape may take on the form universally known as a comma, the concavity of which, for example, at rest, is pointing opposite the spinning direction of the first roller (21) as will appear subsequently. Another paddle shape (27) is illustrated in FIG. 56 and, when viewed as a straight transversal cross section, is in the shape of an uppercase L, the base of which is at the free end of the paddle. Each of these shapes produces a massage with a different intensity and effect.

The second roller (22) has a smooth type outer surface that protrudes from the application surface (S) or that extends to the side of the application surface (S).

Above we defined a smooth type surface. As illustrated in FIGS. 50 to 54, the smooth type surface of the roller (22) may be absolutely smooth. FIG. 55 illustrates an alternative roller with a smooth type surface: the surface is fluted parallel to the height of the roller, in a regular fashion. Thus, when the roller is in contact with the skin, it defines a pressure angle (Sa), of which one can consider at least approximately half of the exterior surface contained within the pressure angle (Sa) of the roller toward the skin is in contact with the skin.

In the invention, the massaging head (1) also has a means of transmission (30) designed to propel the rollers (21 and 22) simultaneously in the same direction, going from the exterior of the work zone toward the interior of the work zone, for the first roller, and from the interior toward the exterior of the work zone for the second roller, viewed from the exterior of the massaging head as indicated by Arrows F1 and F2. The transmission means (30) is thus designed to cooperate with the driving means (7) and more specifically with the output shaft (8), so as to transmit and transform the rotation movement of the electric motor along the longitudinal axis (L) into spinning movements along Axes Δ and Δ', which are in an orthogonal direction to that of the longitudinal axis (L).

Figure 52:
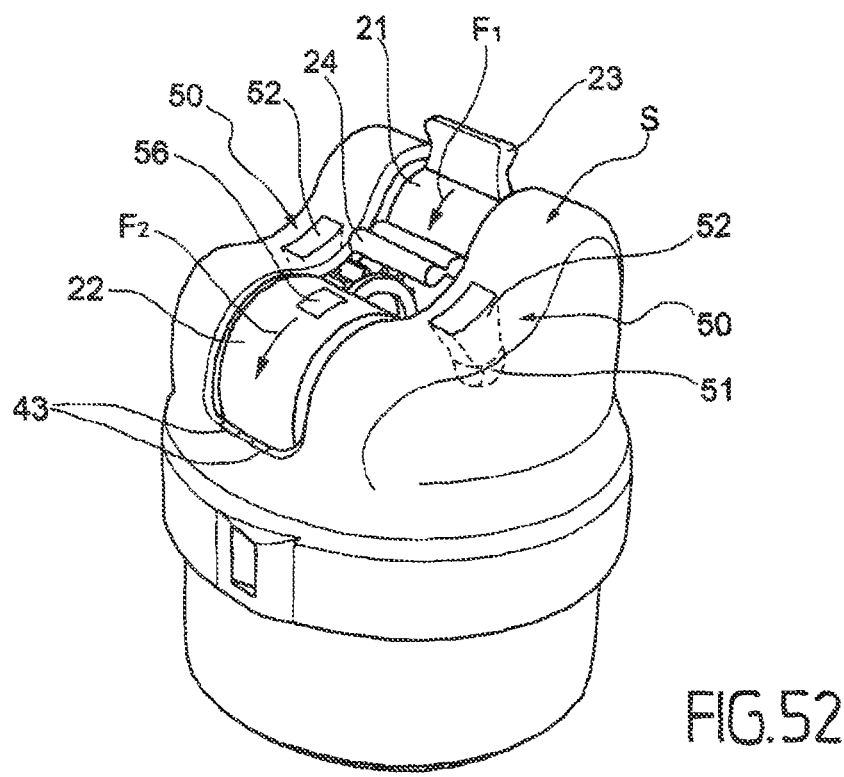

In the example illustrated and as shown in FIG. 52, the transmission means (30) includes a gear train with, first, two truncated conic pinions providing an angle transmission and, then, straight pinions that drive the massaging rollers (21 and 22) together, at different speeds.

The transmission means (30) is preferably designed to produce a spin speed of the first roller (21) that is greater than that of the second roller (22) and in this case, double that of the second roller (22).

The massaging appliance thus created is implemented as follows. The application surface (S) is placed against the face, and then the user starts the massaging appliance (A) using the interface (11). The massaging rollers (21 and 22) then begin spinning in the same direction. The spinning of the second roller (22) causes the movement of the massaging head over the skin, while the paddles of the first roller (21) release the skin successively, as the massaging head advances.

Figure 51:
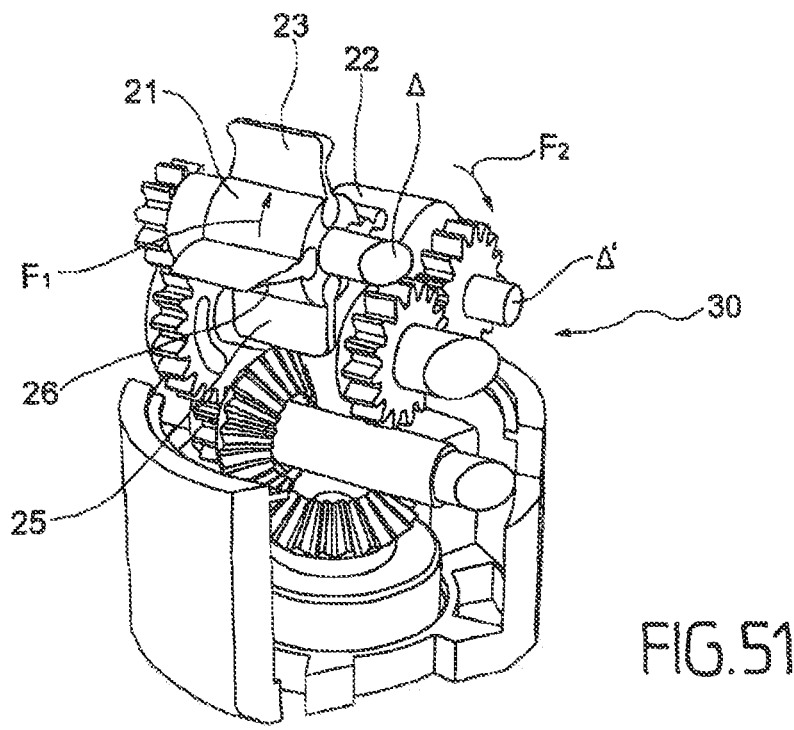

The massage performed using the appliance described in the invention can reduce wrinkles by stimulating the blood circulation in the skin of the face, or even the skin of the neck. In order to optimize this treatment, the massaging appliance (A) as illustrated in FIGS. 50 to 52, includes a means (40) of applying a cosmetic product. In the example illustrated, the means of applying the cosmetic product (40) includes a reservoir (41) located in the drive unit (2) and connected, via a sampling pump (42), to two dispensing nozzles (43) located on the application surface (S) and more specifically in the immediate proximity of the second massaging roller (22), as shown in FIG. 51. Thus, the cosmetic product is applied to the skin by the second massaging roller. The sampling pump (42) is operated by the control unit (10) such that the cosmetic product is dispensed as the massaging appliance (A) is operating.

Of course, the application surface (S) could have only one dispensing nozzle or even several dispensing nozzles positioned differently. Likewise, the cosmetic product dispensing nozzle(s) could be positioned inside the massaging head (1), so as to apply the cosmetic product on either massaging roller, or even both massaging rollers.

Moreover, still in the example illustrated in FIGS. 50 to 52, the massaging appliance (A) also has a means of applying an electrical current (45) that includes a unit (46) that generates an electrical current and/or voltage. The generator unit (46) is operated by the control unit (10). The generator unit (46) is connected, via a system of brushes (47) to an electrode (56) formed at least partially by the conductive surface of the second roller (22).

When the massaging appliance (A) is in use, the control unit (10) operates the generator unit (46) such that, for example, a microcurrent is applied to stimulate the skin or the muscles of the face, or even an electrophoresis phenomenon is induced, thereby promoting the assimilation of the active principles of the cosmetic product.

In the example illustrated in FIGS. 50 to 52, the massaging head (1) has a means (50) of diffusing light toward the face. In this case, the means of diffusion (50) is positioned in the massaging head, and more specifically the application surface (S). The means of diffusion (50) has, as its light source, two electroluminescent diodes (51) operated by the control unit (10) and placed on either side of the work zone (Z). These light sources (51) are then each combined with an optical system (52) formed by a transparent block that forms a light guide and includes a light output surface on the pressure surface (S) and is therefore intended to be pointed toward the face of the person using of the massaging appliance (A) described in the invention.

Figure 53:
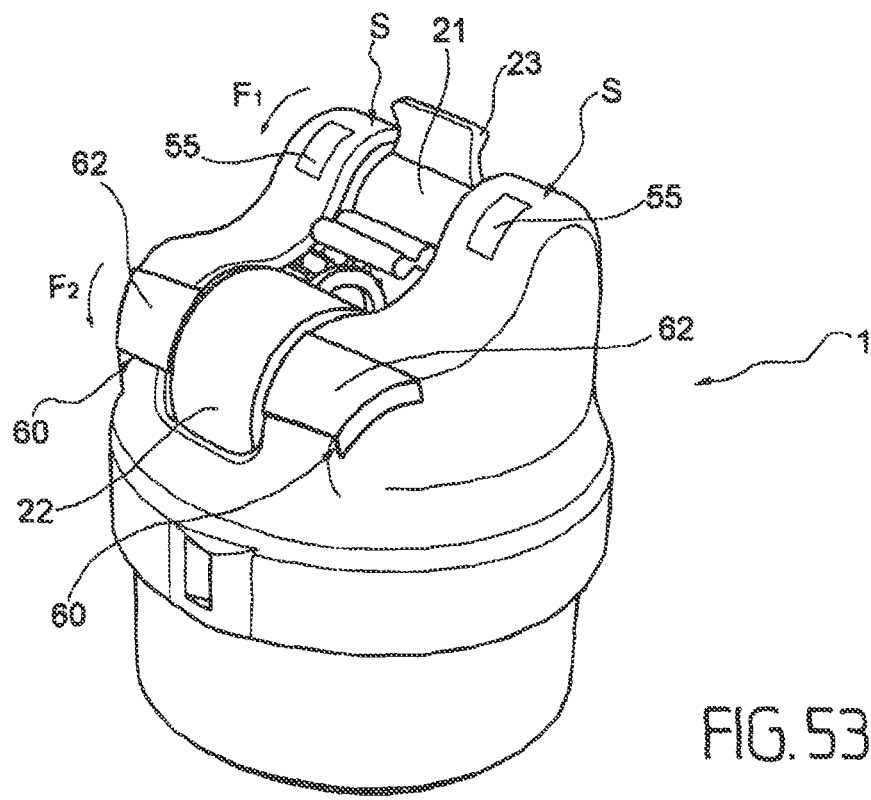
Figure 54:
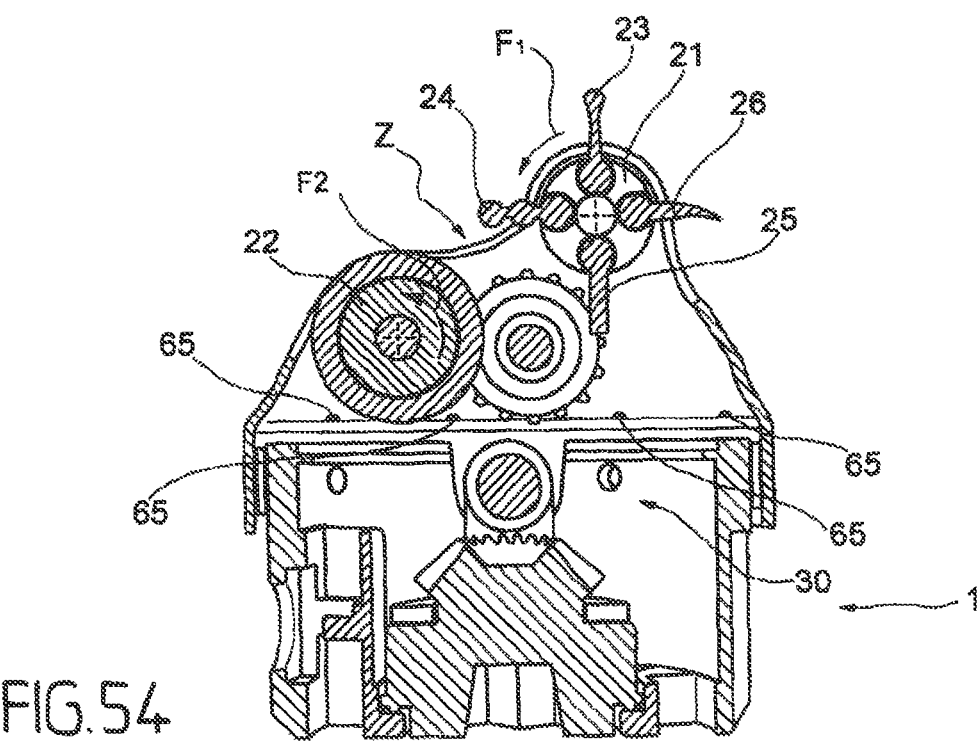
Figure 55:
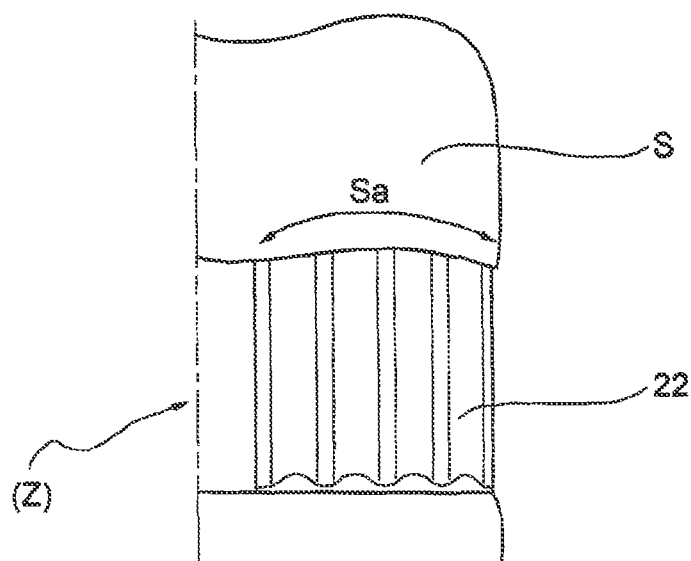

FIGS. 53 and 54 depict one implementation variant of a massaging head for a massaging appliance described in the invention, which differs from the one described in reference to FIGS. 50 to 52, in that the application surface (S) has two electrodes (55) connected to the electric current generator unit (46).

Still in reference to this example of implementation, the massaging head (1) also has, as its means of dispensing a cosmetic product, two caps (60) designed to be removable, on said massaging head (1). Each cap (60) thus has a pad (62) soaked with cosmetic product.

Moreover, in this variant, the means of diffusion (50) is located in the massaging head and includes, as its source of light, electroluminescent diodes (65) operated by the control unit (10). The electroluminescent diodes (65) light up the inside of the massaging head (1), such that the massage zone forms a light output surface. In this regard, the upper portion of the massaging head could also be transparent, such that the application surface (S) would form a light output surface.

Of course, various other modifications or variants of the massaging head described in the invention could be considered within the scope of the attached claims.

Of course, each of the heads described here is equipped with the distinguishing system.

While operating, several programs, such as "anti-aging, anti-wrinkles, rejuvenating and sculpting," are offered via the UI as follows. The session may consist of a series of different massages, simultaneously combined with warm, intense light (orange-red), each head being designed for a particular zone and a particular action, and preferably with 5 to 10 minutes per head.

Alternatively, the session may consist of a series of different massages before or after the application of warm, intense light (orange-red). In a first example, the first phase can be a "heat, skin preparation" program. It includes a gradual warming and continual temperature measurements (via a temperature sensor connected to the control means), and when the temperature value is reached (a threshold of between 37° C. and 45° C., and preferably 41° C.), the appliance indicates, via the UI in a visual display, as a light or even a sound or vibration, that the user can begin the program on the skin; a timer may then be initiated and a thermostat can be programmed to maintain the target temperature. This prepares the skin for the massage, dilates the blood vessels and awakens the fibroblasts. In a second example, the last phase can be a "heat" program. This promotes elimination and drainage and supports well-being at the end of the treatment. This improves the comfort and efficacy of the treatment. The heat can be produced by infrared LEDs, by LED radiators or by one or more flat heating elements (ILO channel), by resistance with the mechanical conduction elements through serigraphed channels.

As stated above, the heat can also be programmed simultaneously with a motorized mechanical anti-aging type massage.

The appliance distinguishes the head attached to the body, sets the parameters of the motor (voltage for speed and current limit in case of pinching) and of the light. It indicates when the head must be changed (for example, after six minutes). The "tapping" head is recommended for around the eyes (slightly lower light intensity) to, on the one hand, stimulate microcirculation and thus reduce circles/bags, and on the other hand, to activate the metabolism in the lines to re-initiate the production of the structural elements of the skin and fill in wrinkles and fine lines. The "interior work zone" head with three massaging balls is recommended for broad areas, for deep kneading, and to stimulate fibroblasts and microcirculation. The "Jacquet pinching" head has two rollers, one of which has a surface that is referred to as smooth, and the other with paddles, is recommended to stimulate lines in order to fill in wrinkles. The "double roller" head with two rollers spinning in inverse synchronicity, is recommended for deep massaging to sculpt the features of the face. The automatic adjustment of the parameters is controlled according to software installed on the microcontroller.

In addition, the application of a cosmetic product, by hand or with the built-in product dispensing system, is optional, and can be offered before or after a massage. The dispensing of the cosmetics will be manual or automatic, depending on the head chosen, and it can be done during the massage for better penetration of the cosmetic; it can be done prior to the massage to lubricate the contact, for better sliding and less friction and irritation; it can be done after the massage for adequate hydration and effective anti-aging activity; it can be done before or at the same time as the application of light for light activation and/or decreased light loss due to better absorption of the light in the skin (less reflection to the interface); it can be done after heating for better penetration of the active ingredients in the skin.

For each treatment, a progressive massage speed or frequency can also be proposed during operation. This allows the skin to gradually become accustomed and offers greater comfort, and then the massage intensifies for greater efficacy once the skin is "awake." This is managed by the microcontroller and timer (quartz oscillator).

The invention claimed is:

1. Massaging appliance comprising:
a body with a driving means,
at least one type of massaging head that includes at least two massaging elements,
a transmission mechanism that activates the massaging elements via the propulsion of the driving means,
a means of attachment that is configured to attach, in a removable manner, at least one type of massaging head to the body,
a means of distinguishing the type of massaging head attached to the body, and a control means of said massaging appliance, which, depending on the type of massaging head distinguished, is configured to act upon the driving means, so as to control the movement of at least two elements in the massaging head.

2. Massaging appliance described in claim 1, in which the control means of said massaging appliance is configured to act upon the driving means, so as to control, in a coordinated manner, a movement of said at least two massaging elements.

3. Massaging appliance described in claim 1, in which the control means of said massaging appliance is configured to act upon the driving means so as to activate the spinning of each of said at least two massaging elements.

4. Massaging appliance described in claim 1, in which the massaging elements are chosen from among the set consisting of: massaging tip, massaging finger, massaging roller, work head, massaging ball.

5. Massaging appliance described in claim 1, in which the control means of said massaging appliance is configured to act upon the driving means, so as to control at least one of the following parameters of said at least two massaging elements: spin speed, spin direction and oscillation frequency.

6. Massaging appliance described in claim 1, with a means of emitting waves, and in which the control means is configured to act upon the wave-emitting means depending on the type of massaging head attached to the body.

7. Massaging appliance described in claim 6, in which the wave-emitting means is a means of emitting light waves among at least one of the following wavelengths: visible wavelengths, including red and orange, and an infrared wavelength.

8. Massaging appliance described in claim 7, in which the control means is configured to act upon the wave-emitting means and modify the wavelength(s) and/or intensity and/or frequency of wave emission, depending on the type of massaging head attached to the body.

9. Massaging appliance described in claim 8, wherein wave emitting means is located on the body and includes a means of transferring the waves, from the wave emitting means to the massaging head.

10. Massaging appliance described in claim 6, in which the wave-emitting means includes electroluminescent diodes.

11. Massaging appliance described in claim 6, in which the control means is configured to act simultaneously upon the wave-emitting means and on the driving means, so as to control the movement of at least two elements of the massaging head, and to do so depending on the type of massaging head distinguished, to establish at least two different phases of skin treatment during the treatment.

12. Massaging appliance described in claim 1, in which the distinguishing means consists of mechanical, magnetic or optical sensors located on at least one type of massaging head and the body, and is configured to transmit information to the control means depending on the type of massaging head attached to the body.

13. Massaging appliance described in claim 1, having a cosmetic product dispensing system located on the body, and a means of transfer of the product, from the body to the massaging head.

14. Massaging appliance described in claim 13, in which the control means is configured to act upon the cosmetic product dispensing system and to modify at least the dispensing of the cosmetic product depending on the type of massaging head attached to the body.

15. Massaging appliance described in claim 1, with a massaging head that includes:
an application surface and,
in which the massaging elements consist of two massaging rollers positioned along two parallel longitudinal axes, with a gap between them, and partially extending beyond the exterior of the application surface, and
in which a transmission mechanism is configured to spin the two rollers in an inverse synchronized manner, such that, when viewed along a plane perpendicular to the two axes, the portion of the massaging roller located on the left, which extends beyond the application surface, spins in the trigonometric direction, and the portion of the massaging roller located on the right that extends beyond the application surface, spins clockwise.

16. Massaging appliance described in claim 1, with a massaging head that includes:
two massaging elements consisting of two parallel massaging rollers that can spin on themselves along two axes of rotation that are parallel to one another and to an application surface (S), separated from one another by a work zone (Z), a first roller having at least one paddle that extends radially to protrude from the surface of the first roller, and wherein the second roller has a smooth surface,
the transmission mechanism that spins the rollers in the same direction, the first roller going from an exterior of the work zone (Z) toward an interior of the work zone (Z), and the second roller going from the interior of the work zone toward the exterior of the work zone, as viewed from an exterior of the massaging head.

17. Massaging appliance described in claim 6, with a massaging head that includes:
a pressure element intended to be pressed against the face of a user and that defines a pressure surface (S),
above the pressure element at least one massaging element consisting of a massaging finger, each finger having a work head intended to come into contact with the face, and each finger being able to move between:
a position of retraction (R), in which the work head is located below the pressure surface (S) toward the interior of the massaging head,
a position of extension (E), in which the work head is located above the pressure surface (S) toward the exterior of the massaging head,
a means of maneuvering each massaging finger to be connected to the transmission mechanism and designed to move each of the massaging fingers between its positions of extension (E) and retraction (R) in an alternating manner.

18. Massaging appliance described in claim 17, in which the control means is configured, upon distinguishing the head, to activate a visible orange light wave emitting system.

19. Massaging appliance described in claim 6, with a massaging head that includes:
a pressure element that is intended to come into contact with the face and that forms a pressure crown defining, on the one hand, a pressure surface (S) within a pressure plane (P) and, on the other hand, a work zone (Z) located inside the pressure crown,
inside the pressure crown and in the work zone (Z), at least one massaging element consisting of a work head with a work surface protruding from the pressure plane (P),
a maneuvering means to be connected to the transmission mechanism and designed to spin each work head along at least one axis of rotation ($\Delta$, $\Delta'$), offset from the center of a corresponding work surface (T).

20. Massaging appliance described in claim 19, in which the control means is configured, upon distinguishing the head, to activate an infrared light wave emitting system.

21. Massaging appliance described in claim 1, having a transcutaneous iontophoresis treatment device, which is configured to transmit to the skin, while said massaging appliance is applied, a current that improves and/or accelerates the penetration of a cosmetic product.

* * * * *